(12) United States Patent
Dai et al.

(10) Patent No.: US 12,227,491 B2
(45) Date of Patent: Feb. 18, 2025

(54) EGFR INHIBITORS

(71) Applicant: INVENTISBIO CO., LTD., Shanghai (CN)

(72) Inventors: Xing Dai, Shanghai (CN); Yueheng Jiang, Shanghai (CN)

(73) Assignee: INVENTISBIO CO., LTD., Shanghai (CN)

( * ) Notice: Subject to any disclaimer, the term of this patent is extended or adjusted under 35 U.S.C. 154(b) by 0 days.

(21) Appl. No.: 18/187,430

(22) Filed: Mar. 21, 2023

(65) Prior Publication Data

US 2023/0331703 A1   Oct. 19, 2023

Related U.S. Application Data

(63) Continuation of application No. 17/046,621, filed as application No. PCT/CN2019/086748 on May 14, 2019, now Pat. No. 11,639,344.

(60) Provisional application No. 62/678,634, filed on May 31, 2018.

(30) Foreign Application Priority Data

May 15, 2018  (WO) ................ PCT/CN2018/086829

(51) Int. Cl.
| | | |
|---|---|---|
| *C07D 403/04* | (2006.01) | |
| *A61K 9/20* | (2006.01) | |
| *A61K 9/48* | (2006.01) | |
| *A61K 31/506* | (2006.01) | |

(52) U.S. Cl.
CPC ............ *C07D 403/04* (2013.01); *A61K 9/20* (2013.01); *A61K 9/48* (2013.01); *C07B 2200/13* (2013.01)

(58) Field of Classification Search
CPC ...... C07D 403/04; A61K 31/506; A61P 35/00

USPC ............................................ 544/331; 514/275
See application file for complete search history.

(56) References Cited

U.S. PATENT DOCUMENTS

| | | |
|---|---|---|
| 10,179,784 B2 | 1/2019 | Jiang |
| 10,376,512 B1 | 8/2019 | Wang et al. |
| 2017/0355696 A1 | 12/2017 | Jiang |
| 2019/0092746 A1 | 3/2019 | Butterworth et al. |
| 2019/0152969 A1 | 5/2019 | Jiang |

FOREIGN PATENT DOCUMENTS

| | | |
|---|---|---|
| CA | 2966376 | 5/2016 |
| CN | 103702990 | 4/2014 |
| CN | 105085489 | 11/2015 |
| CN | 106478605 | 3/2017 |
| CN | 106699736 | 5/2017 |
| CN | 107522690 | 12/2017 |
| CN | 107973782 A | 5/2018 |

OTHER PUBLICATIONS

International Search Report for PCT/CN2019/086748 dated Aug. 21, 2019, 6 pages.
Written Opinion of the ISA for PCT/CN2019/086748 dated Aug. 21, 2019, 5 pages.

*Primary Examiner* — Charanjit Aulakh
(74) *Attorney, Agent, or Firm* — NIXON & VANDERHYE, PC

(57) ABSTRACT

Provided herein are compounds, salts, solid forms, and pharmaceutical compositions that are related to EGFR inhibitors, such as N-(2-((2-(dimethylanino)ethyl)(methyl)amino)-4-methoxy-5-((4-(1-(2,2,2-trifluoroethyl)-1H-indol-3-yl)pyrimidin-2-yl)amino)phenyl)acrylamide, as well as methods of preparing the same. Also provided herein are methods of using the compounds, salts, solid forms, and pharmaceutical compositions for the treatment of diseases or disorders, such as cancer.

20 Claims, 8 Drawing Sheets

| # | RT | Heigh | Area | Area% |
|---|------|------------|------------|-------|
| 1 | 8.84 | 0.41622 | 2.33180 | 0.03 |
| 2 | 9.17 | 0.65191 | 3.53271 | 0.05 |
| 3 | 10.45 | 1255.41431 | 6683.22461 | 99.24 |
| 4 | 10.86 | 0.41842 | 3.12245 | 0.05 |
| 5 | 11.10 | 0.71965 | 3.39795 | 0.05 |
| 6 | 11.79 | 0.57373 | 2.59179 | 0.04 |
| 7 | 14.34 | 0.45437 | 2.79166 | 0.04 |
| 8 | 16.41 | 0.35017 | 2.56116 | 0.04 |
| 9 | 16.79 | 0.35565 | 1.91854 | 0.03 |
| 10 | 17.49 | 0.73376 | 3.51791 | 0.05 |
| 11 | 18.55 | 1.48514 | 5.17649 | 0.08 |
| 12 | 19.23 | 2.28738 | 8.17456 | 0.12 |
| 13 | 19.79 | 0.77597 | 3.69555 | 0.05 |
| 14 | 23.67 | 0.19106 | 1.36517 | 0.02 |

EGFR INHIBITORS

This application is a continuation of U.S. Ser. No. 17/046,621 filed Oct. 9, 2020, which is the U.S. national phase of International Application No. PCT/CN2019/086748 filed May 14, 2019 which designated the U.S. and claims priority to International Application No. PCT/CN2018/086829 filed May 15, 2018 and U.S. Provisional Patent Application No. 62/678,634 filed May 31, 2018, the entire contents of each of which are hereby incorporated by reference.

BACKGROUND OF THE INVENTION

Field of the Invention

In various embodiments, the present invention generally relates to EGFR inhibitors, pharmaceutical compositions comprising the same, and methods of preparation and use thereof.

Background Art

Epidermal growth factor receptor (EGFR) is a receptor tyrosine protein kinase, and a transmembrane protein in the ErbB receptor family.

EGFR regulates proliferation, survival, adhesion, migration and differentiation of cells, which is hyperactivated or sustained in a variety of tumor cells, such as lung cancer cells, breast cancer cells, prostate cancer cells and the like. Abnormal activation of EGFR plays a key role in tumor transformation and growth. Blocking activation of EGFR has been clinically proven as one of the effective targeted therapies for treating cancer. EGFR has been found to be expressed in 50% of NSCLC (non-small cell lung cancer) patients, which makes EGFR and its family member candidates for targeted therapy. Gefitinib and erlotinib are the first generation of small molecule inhibitors of EGFR, which are primarily used as drugs for treating advanced NSCLC. Clinical results show that gefitinib or erlotinib has effect in about 10% of Caucasian patients with NSCLC and about 35% of Asian NSCLC patients. Analyses also show that the response rate to EGFR-tyrosine kinase inhibitor (TKI) in most NSCLC patients with EGFR activated mutants was significantly higher than that in NSCLC patients with only wild type EGFR.

Clinical studies have further shown that many patients soon (12-14 months) became resistant to these small molecule inhibitors of EGFR, i.e., acquired drug resistance. Gatekeeper residue mutation, T790M mutation, occurs in EGFR exon 20, which is one of the major mechanisms leading to drug resistance. New generation of inhibitors for these EGFR mutants have recently been successful. Afatinib is a potent and irreversible double inhibitor of EGFR and human epidermal growth factor receptor 2 (HER2) tyrosine kinases. Other similar multi-target, highly active and irreversible inhibitors, such as canertinib, and dacomitinib were also in clinical trials. These novel second-generation irreversible inhibitors have a strong inhibitory effect on EGFR with L858R and T790M mutants, and have a significant effect on gefitinib or erlotinib-resistant cancer patients. However, these second-generation EGFR mutant inhibitors also have a strong inhibitory effect on wild-type EGFR (WT-EGFR). Clinical studies have shown that inhibition of wild-type EGFR can lead to drug toxicity and side effects in most patients, such as rash or diarrhea in the human body.

In order to overcome the toxicity and side effects of the second-generation EGFR inhibitors, it is desired to reduce the inhibitory effect on wild-type EGFR (WT-EGFR). A third generation of EGFR inhibitors should retain a strong inhibition against EGFR L858R mutants, Exon19 deletion mutants and/or T790M mutants, with a relatively low inhibitory effect on WT-EGFR and other tyrosine protein kinase receptors. Such compounds can be used not only in the treatment of cancer patients with a resistance to EGFR L858R mutants and Exon19 deletion mutants, but also in the treatment of cancer patients with EGFR-T790M mutants. One of the third-generation EGFR inhibitors, AZD9291, has a beneficial clinical effect. But its major metabolite, AZ5104, has a strong inhibitory effect on wild-type EGFR (WT-EGFR), which may induce most of the common side effects such as a clinically common rash, diarrhea and the like.

BRIEF SUMMARY OF THE INVENTION

U.S. Publication No. 2017/0355696 A1 describes various pyrimidine compounds that are effective in selectively inhibiting EGFR variant(s) or mutant(s) and are useful in treating diseases or disorders mediated by such EGFR variant(s) or mutant(s) such as cancer. In various embodiments, the present invention is directed to EGFR inhibitors and pharmaceutically acceptable salts thereof, for example, in a crystalline form and/or as a substantially pure compound, pharmaceutical compositions comprising the same, methods of preparing the same, and methods of using the same.

Certain embodiments of the present invention are directed to Compound 4 (N-(2-((2-(dimethylamino)ethyl)(methyl)amino)-4-methoxy-5-((4-(1-(2,2,2-trifluoroethyl)-1H-indol-3-yl)pyrimidin-2-yl)amino)phenyl)acrylamide), or its pharmaceutically acceptable salt.

Some embodiments of the present invention are directed to a method of preparing Compound 4, or a pharmaceutically acceptable salt thereof. In some embodiments, the method comprises:

(1) converting Compound 1, or a salt thereof, into a compound of Formula III, or a salt thereof, under an amide formation condition, wherein Lg in Formula III is a leaving group;

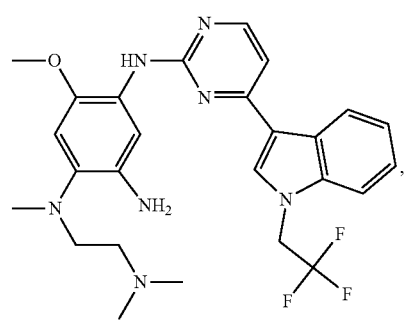

1

-continued

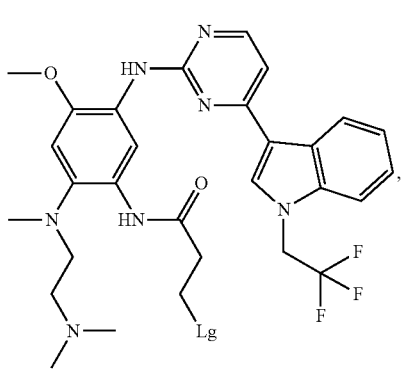

Formula III and (2) converting the compound of Formula III, or a salt thereof, into Compound 4 under an elimination reaction condition. In some embodiments, the method further comprises reacting Compound 4 with a suitable acid to form a pharmaceutically acceptable salt of Compound 4. In some embodiments, the Lg in Formula III is a halide or an oxygen containing leaving group, e.g., Lg in Formula III can be Cl. In some embodiments, converting Compound 1 into the compound of Formula III, or a salt thereof, comprises reacting Compound 1 with an acyl chloride reagent having Formula IV,

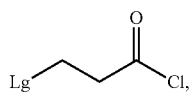

wherein Lg is a leaving group, e.g., Cl. In some embodiments, converting the compound of Formula III, or a salt thereof, into Compound 4 comprises contacting the compound of Formula III with a base (e.g., an alkali base such as KOH). Compound 1 can be prepared by various methods, e.g., as described herein.

Compound 4 can be prepared in high purity according to the process disclosed herein. Typically, Compound 4 prepared according to the processes herein has a total impurity of less than 2% (e.g., less than 1.5%, less than 1%, less than 0.8%, less than 0.5%, less than 0.2%) as measured by HPLC. In some embodiments, Compound 4 does not contain a single impurity in an amount greater than 1% (e.g., not greater than 0.8%, not greater than 0.5%, not greater than 0.2%) as measured by HPLC.

In some embodiments, the present disclosure provides Compound 4, or a pharmaceutically acceptable salt, produced by any of the synthetic methods herein. In some embodiments, the present disclosure is directed to a substantially pure Compound 4, or a pharmaceutically acceptable salt thereof. In some embodiments, the Compound 4 has a purity by HPLC of at least 95% (e.g., about 96%, about 97%, about 98%, about 98.5%, about 99%, or above 99%). In some embodiments, the Compound 4 can be substantially free of an impurity characterized by an HPLC relative retention time of about 1.02 (impurity A). In some embodiments, the Compound 4 can be substantially free of an impurity characterized by an HPLC relative retention time of about 0.88 (impurity B).

In some embodiments, the present disclosure is directed to a substantially pure pharmaceutically acceptable salt of Compound 4. Typically, a substantially pure pharmaceutically acceptable salt of Compound 4 can be prepared by mixing the substantially pure Compound 4 with a suitable acid (e.g., HCl, methanesulfonic acid, etc.). In some embodiments, the substantially pure pharmaceutically acceptable salt of Compound 4 can be a substantially pure mesylate salt of Compound 4, for example, a monomesylate of Compound 4, named herein as Compound 5.

Compound 5 described herein can be substantially pure. For example, Compound 5 can be characterized by a purity by weight and/or by HPLC area of least 70% (e.g., at least 75%, at least 80%, at least 85%, at least 90%, at least 95%, at least 97%, or at least 99%). In some embodiments, the substantially pure Compound 5 can be characterized as having an amount of methanesulfonic acid close to the theoretical methanesulfonic acid content calculated based on the formula of Compound 5. In any of the embodiments described herein, the substantially pure Compound 5 can comprise, consist essentially of, or consist of Compound 5 in Form I as described herein. In some embodiments, Form I of Compound 5 can be characterized by its particle size distribution, e.g., as described herein.

In some embodiments, the present invention provides a pharmaceutical composition comprising Compound 4 (e.g., a substantially pure Compound 4 herein) or a pharmaceutically acceptable salt thereof, such as a mesylate salt. In some embodiments, the present invention provides a pharmaceutical composition comprising, consisting essentially of, or consisting of the substantially pure Compound 4, or a pharmaceutically acceptable salt thereof, e.g., Compound 5, and optionally a pharmaceutically acceptable excipient or carrier.

The pharmaceutical compositions described herein can be formulated for any suitable routes of administration. In some embodiments, the pharmaceutical composition can be formulated for oral administration. For example, in any of the embodiments described herein, the pharmaceutical composition can be formulated in the form of a tablet or a capsule. In some embodiments, the pharmaceutical composition can be enteric coated. However, in some embodiments, the pharmaceutical composition can be non-enteric coated.

Certain embodiments of the present invention are directed to methods of using the compounds, salts, solid forms, and/or pharmaceutical compositions herein for treating various diseases or disorders in a subject in need thereof. In some embodiments, the disease or disorder is mediated by EGFR variant(s) or mutant(s), such as an L858R mutant, Exon19 deletion mutant, and/or T790M mutant. In some embodiments, the present invention provides a method of treating cancer. In some embodiments, the cancer is ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular carcinoma, gastrointestinal stromal tumor, thyroid cancer, cholangiocarcinoma, endometrial cancer, kidney cancer, anaplastic large cell lymphoma, acute myeloid leukemia, multiple myeloma and/or mesothelioma. In some embodiments, the cancer is lung cancer. In some embodiments, the cancer is non-small cell lung cancer. In some embodiments, the subject is characterized as being resistant to one or more EGFR inhibitors, e.g., other than Compound 4 or salts thereof, such as gefitinib, erlotinib, and/or icotinib.

The methods described herein typically comprise administering a therapeutically effective amount of substantially pure Compound 4, or a pharmaceutically acceptable salt thereof, e.g., Compound 5, to the subject. The methods described herein are not limited to any specific routes of administration. For example, in any of the embodiments described herein, the administration can be oral administration.

In any of the embodiments described herein, Compound 4, such as the substantially pure Compound 4, or a pharmaceutically acceptable salt thereof, e.g., Compound 5, can be used in a monotherapy, with the active agent consists or consists essentially of Compound 4 or a pharmaceutically acceptable salt thereof, e.g., Compound 5, which can be in Form I, amorphous form, or a combination thereof. However, in some embodiments, the methods described herein can also be used in combination with other therapies, including with additional active agents. For example, the methods herein can be used in combination with one or more selected from a surgical procedure (e.g., conventional anti-cancer surgical therapy), radiotherapy, chemotherapy and antitumor immunotherapy.

BRIEF DESCRIPTION OF THE DRAWINGS/FIGURES

DETAILED DESCRIPTION OF THE INVENTION

Figure 1:
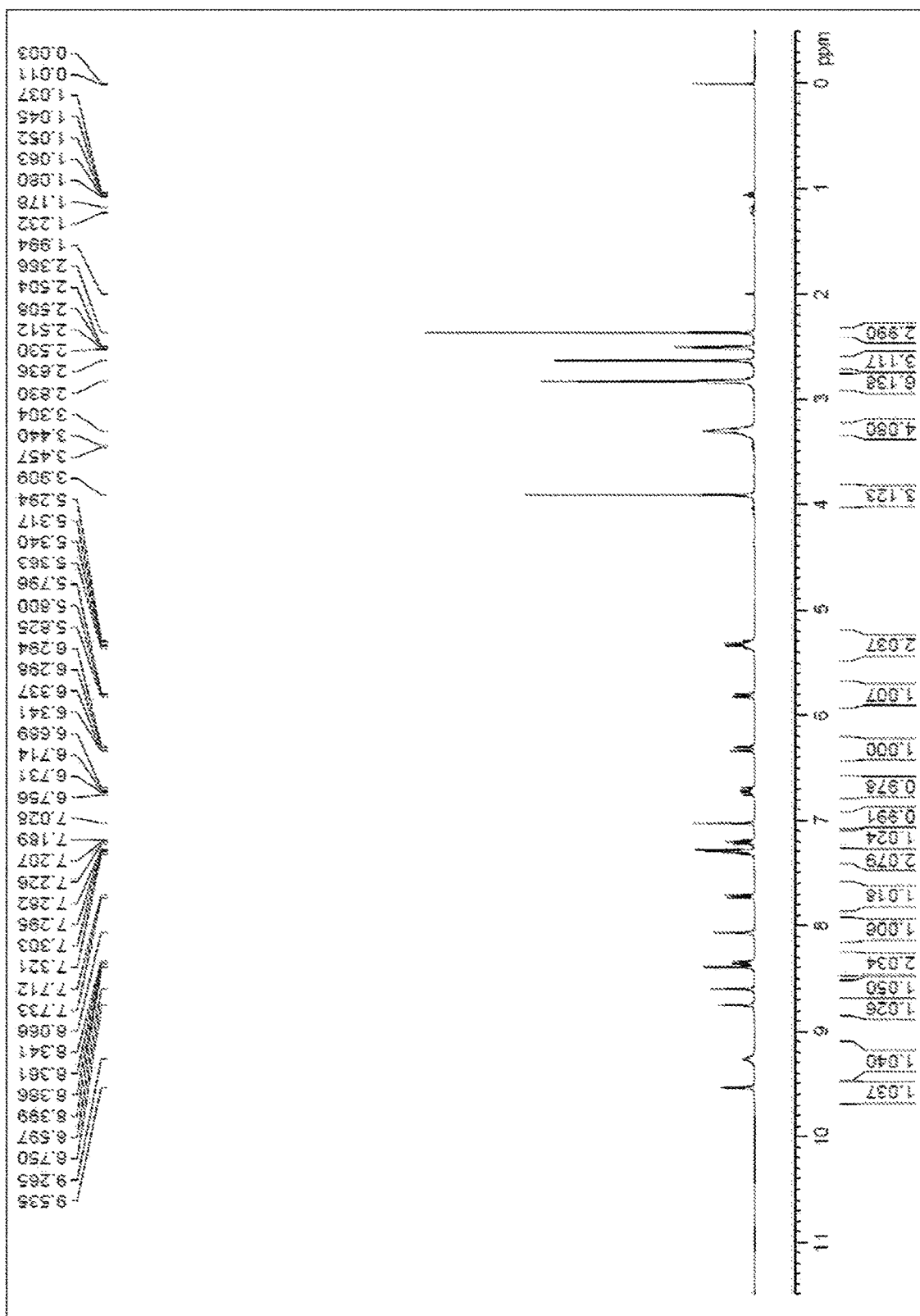
FIG. 1 shows a representative $^1$H NMR spectrum of Compound 5 in d6 DMSO.

In various embodiments, compounds and pharmaceutically acceptable salts, for example, in a crystalline form or as a substantially pure compound, are provided. Also provided are pharmaceutical compositions, methods of preparation, and methods of using the same.

Compounds and Salts

In various embodiments, the present invention is directed to compounds and/or salts (e.g., monomesylate salt) of compounds that are effective inhibitors of EGFR variant(s) or mutant(s) and are useful in treating various diseases and disorders, such as those mediated by EGFR variant(s) or mutant(s). Examples of such compounds were previously described in U.S. Publication No. 2017/0355696 A1 with application Ser. No. 15/524,228, the content of which is hereby incorporated by reference in its entirety.

In some specific embodiments, the present invention provides a substantially pure Compound 4, or a pharmaceutically acceptable salt thereof. In some embodiments, the present invention provides a methanesulfonic acid addition salt of Compound 4. Compound 4 has a chemical name of N-(2-((2-(dimethylamino)ethyl)(methyl)amino)-4-methoxy-5-((4-(1-(2,2,2-trifluoroethyl)-1H-indol-3-yl)pyrimidin-2-yl)amino)phenyl)acrylamide. Compound 4 is a potent and selective inhibitor of EGFR variant(s) or mutant(s) such as Exon19 deletion mutant and/or T790M mutant, and has a structure shown below:

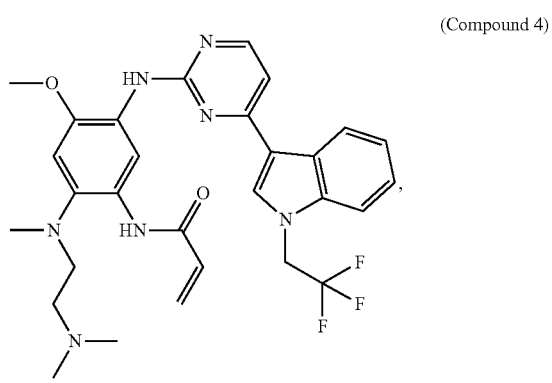 [SMILES: C=CC(=O)Nc1cc(Nc2nccc(-c3cn(CC(F)(F)F)c4ccccc34)n2)c(OC)cc1N(C)CCN(C)C]

(Compound 4)

Compound 4 has more than one basic nitrogen atoms that may form an acid addition salt. In some specific embodiments, the present invention is directed to a monomesylate salt of Compound 4. In some embodiments, the monomesylate salt of Compound 4 is designated herein as Compound 5, represented by the following structure:

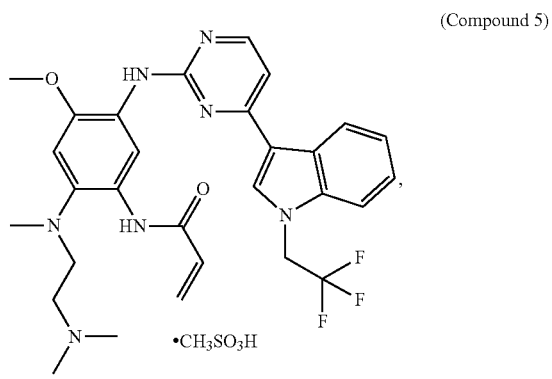

(Compound 5)

For the avoidance of doubt, as used herein, a monomesylate salt of Compound 4 should be understood as a salt formed from the base (Compound 4) and methane sulfonic acid at a molar ratio of 1:1. Those skilled in the art would understand that the precise protonation point of Compound 4 by methane sulfonic acid may vary and in equilibrium among each other. Compound 5 as drawn does not show which nitrogen is protonated, but rather reflects that it is a 1:1 acid addition salt.

Compound 4 can be prepared in high purity according to the process disclosed herein. Typically, Compound 4 prepared according to the processes herein has a total impurity of less than 2% (e.g., less than 1.5%, less than 1%, less than 0.8%, less than 0.5%, less than 0.2%) as measured by HPLC. In some embodiments, Compound 4 does not contain a single impurity in an amount greater than 1% (e.g., not greater than 0.8%, not greater than 0.5%, not greater than 0.2%) as measured by HPLC.

In some embodiments, the present disclosure is directed to a substantially pure Compound 4, or a pharmaceutically acceptable salt thereof. In some embodiments, the Compound 4 has a purity by HPLC of at least 95% (e.g., about 96%, about 97%, about 98%, about 98.5%, about 99%, or above 99%). In some embodiments, the Compound 4 can be substantially free of an impurity characterized by an HPLC relative retention time of about 1.02 (impurity A). For example, in some embodiments, the impurity A can be present in less than 1%, less than 0.8%, less than 0.5%, less than 0.2%, less than 0.1% as measured by HPLC. In some embodiments, the Compound 4 can be characterized by an HPLC trace, which includes a peak representing Compound 4, and a peak representing impurity A, wherein the area percentage of the peak representing impurity A is less than 1%, less than 0.2%, or less than 0.1%. In some embodiments, the Compound 4 can be characterized by an HPLC trace, which includes a peak representing Compound 4, with an area percentage of at least 95% (e.g., about 96%, about 97%, about 98%, about 98.5%, about 99%, or above 99%), wherein the HPLC trace does not include an identifiable peak representing impurity A. In some embodiments, the Compound 4 can be substantially free of an impurity characterized by an HPLC relative retention time of about 0.88 (impurity B). For example, in some embodiments, the impurity B can be present in less than 0.5%, less than 0.2%, or less than 0.1% as measured by HPLC. In some embodiments, the Compound 4 can be characterized by an HPLC trace, which includes a peak representing Compound 4, and a peak representing impurity B, wherein the area percentage of the peak representing impurity B is less than 0.5%, less than 0.2%, or less than 0.1%. In some embodiments, the Compound 4 can be characterized by an HPLC trace, which includes a peak representing Compound 4, with an area percentage of at least 95% (e.g., about 96%, about 97%, about 98%, about 98.5%, about 99%, or above 99%), wherein the HPLC trace does not include an identifiable peak representing impurity B. In some embodiments, the Compound 4 can be substantially free of both impurity A and impurity B, e.g., the combined amount of impurity A and B is less than 0.5%, less than 0.2%, or less than 0.1% as measured by HPLC. In some embodiments, the Compound 4 can be characterized by an HPLC trace, which includes a peak representing Compound 4, a peak representing impurity A, and a peak representing impurity B, wherein the combined area percentage of the peak representing impurity A and the peak representing impurity B is less than 0.5%, less than 0.2%, or less than 0.1%. In some embodiments, the Compound 4 can be characterized by an HPLC trace, which includes a peak representing Compound 4, with an area percentage of at least 95% (e.g., about 96%, about 97%, about 98%, about 98.5%, about 99%, or above 99%), wherein the HPLC trace does not include an identifiable peak representing impurity B, does not include an identifiable peak representing impurity A, or does not include an identifiable peak representing either impurity A or B. In some embodiments, the term "as measure by HPLC" refers to as measured using the HPLC method as shown in Example 1, e.g., using 220 nm as the detection wavelength. In some embodiments, the term "characterized by an HPLC trace" refers to characterized by an HPLC trace obtained by following the HPLC method as shown in Example 1, e.g., using 220 nm as the detection wavelength. An exemplary procedure for preparing Compound 4 is detailed in the Examples section. Representative HPLC traces of Compound 4 purity analysis are shown in the figures.

In some embodiments, the present disclosure is directed to a substantially pure pharmaceutically acceptable salt of Compound 4. Typically, a substantially pure pharmaceutically acceptable salt of Compound 4 can be prepared by mixing the substantially pure Compound 4 with a suitable acid (e.g., HCl, methanesulfonic acid, etc.). The pharmaceutically acceptable salt of Compound 4 can typically be a monosalt, with a molar ratio to the corresponding acid of about 1:1, or a disalt, molar ratio to the corresponding acid of about 1:2 (i.e., about 2 mole of acid per mole of Compound 4). Non-limiting suitable acids include any of those acids that can form a pharmaceutically acceptable acid addition salt with Compound 4. Exemplary suitable acids include 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (L), malonic acid, mandelic acid (DL), methanesulfonic acid, naphthalene-1, 5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p) and undecylenic acid. In some embodiments, the substantially pure pharmaceutically acceptable salt of Compound 4 can be a substantially pure mesylate salt of Compound 4.

The monomesylate salt Compound 5 described herein can be substantially pure. For example, in some embodiments, Compound 5 is characterized by a purity by weight and/or by HPLC area of least 70% (e.g., at least 75%, at least 80%, at least 85%, at least 90%, at least 95%, at least 97%, or at least 99%). In some embodiments, Compound 5 is characterized by a purity by weight and/or by HPLC area of about 70%, about 75%, about 80%, about 85%, about 90%, about 95%, about 97%, about 99%, or any ranges between the specified values. The substantially pure Compound 5 can be prepared from a substantially pure Compound 4. Unless otherwise obvious from context, for the purpose of calculating the weight percentage of the compound/salt in the substantially pure compound or salt, anything other than the compound or salt, or a solvate or hydrate form thereof, is regarded as an impurity, which includes for example residual solvents, moisture contents, etc. For the avoidance of doubt, a composition comprising the substantially pure compound or salt herein and one or more other ingredients should be understood as a composition obtained from directly or indirectly mixing the substantially pure compound or salt herein with the one or more other ingredients, such as water, pharmaceutically acceptable excipients, etc.

The substantially pure Compound 5 described herein can include an amount of methanesulfonic acid close to the theoretical methanesulfonic acid content calculated based on the formula of Compound 5. In some embodiments, the substantially pure Compound 5 is characterized by a methanesulfonic acid content of about 13-15% by weight. Methods for determining methanesulfonic acid content are known, for example, by titration using a Mettler Toledo T50 titrator.

The substantially pure Compound 5 herein can be free or substantially free of Compound 4, and/or can be free or substantially free of other salts of Compound 4. In some embodiments, the substantially pure Compound 5 is substantially free of Compound 4, for example, with an amount of less than 5% by weight (e.g., less than 3%, less than 1%, less than 0.2%, less than 0.1% or less than 0.05%). In some embodiments, the substantially pure Compound 5 is free of Compound 4, other than an amount that may exist through equilibrium. In some embodiments, the substantially pure Compound 5 has no detectable amount of Compound 4. In some embodiments, the substantially pure Compound 5 is substantially free of other salts of Compound 4, such as a bismesylate salt, for example, with an amount less than 5% by weight (e.g., less than 3%, less than 1%, less than 0.2%, less than 0.1% or less than 0.05%). In some embodiments, the substantially pure Compound 5 includes no detectable amount of other salts of Compound 4. In some embodiments, the substantially pure Compound 5 is free of a bismesylate salt of Compound 4, other than an amount that may exist through equilibrium.

Compound 5 can exist in various solid states. For example, in some embodiments, Compound 5 can be in a crystalline form. In some embodiments, Compound 5 can be an amorphous solid. In some embodiments, Compound 5 can be in a mixture of a crystalline form and an amorphous form.

In some specific embodiments, the present invention provides crystalline Form I of Compound 5, the only identifiable stable crystalline form.

Figure 2A:
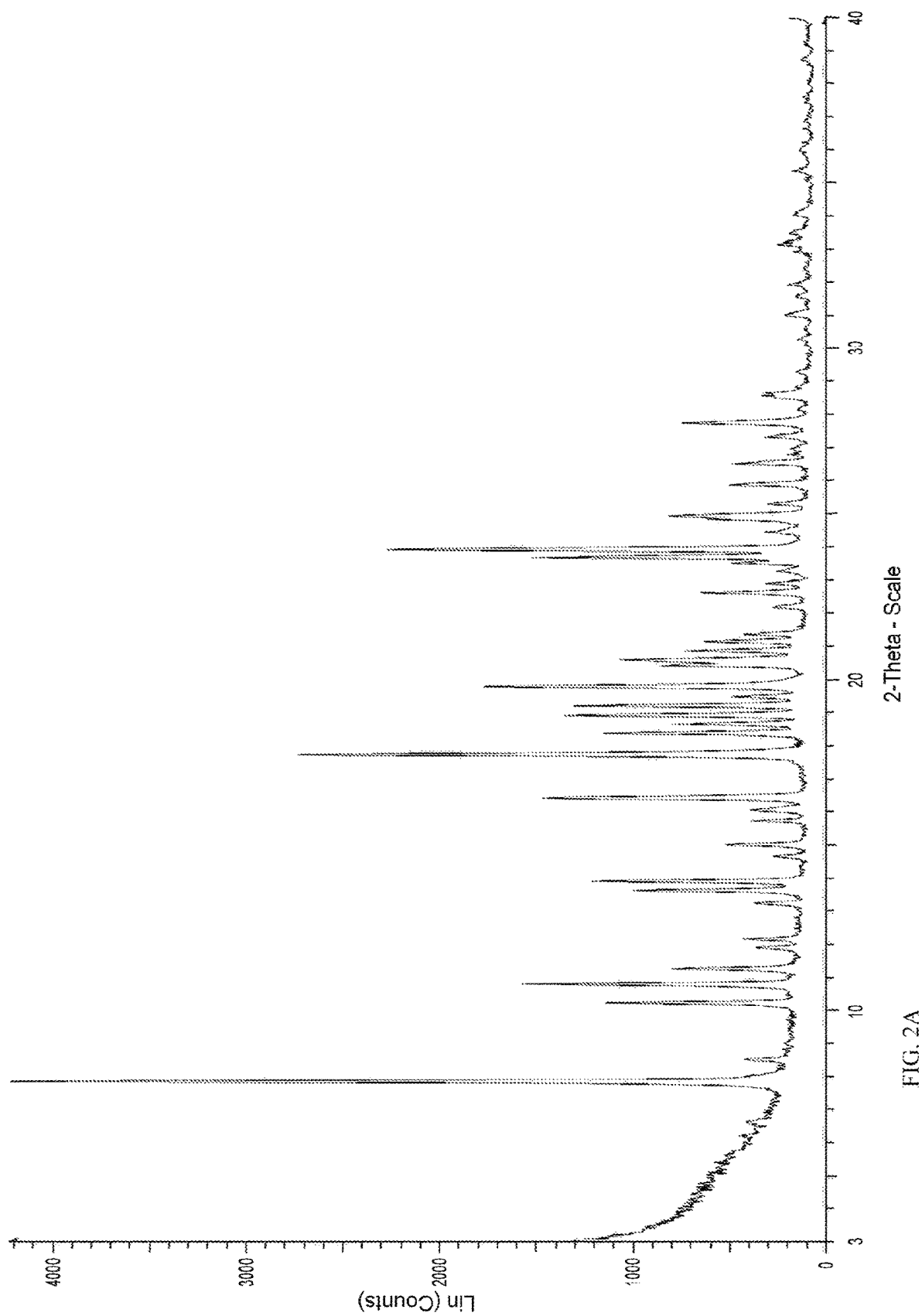
FIG. 2A shows a representative X-ray powder diffraction (XRPD) spectrum of crystalline form I of Compound 5.
Figure 2B:
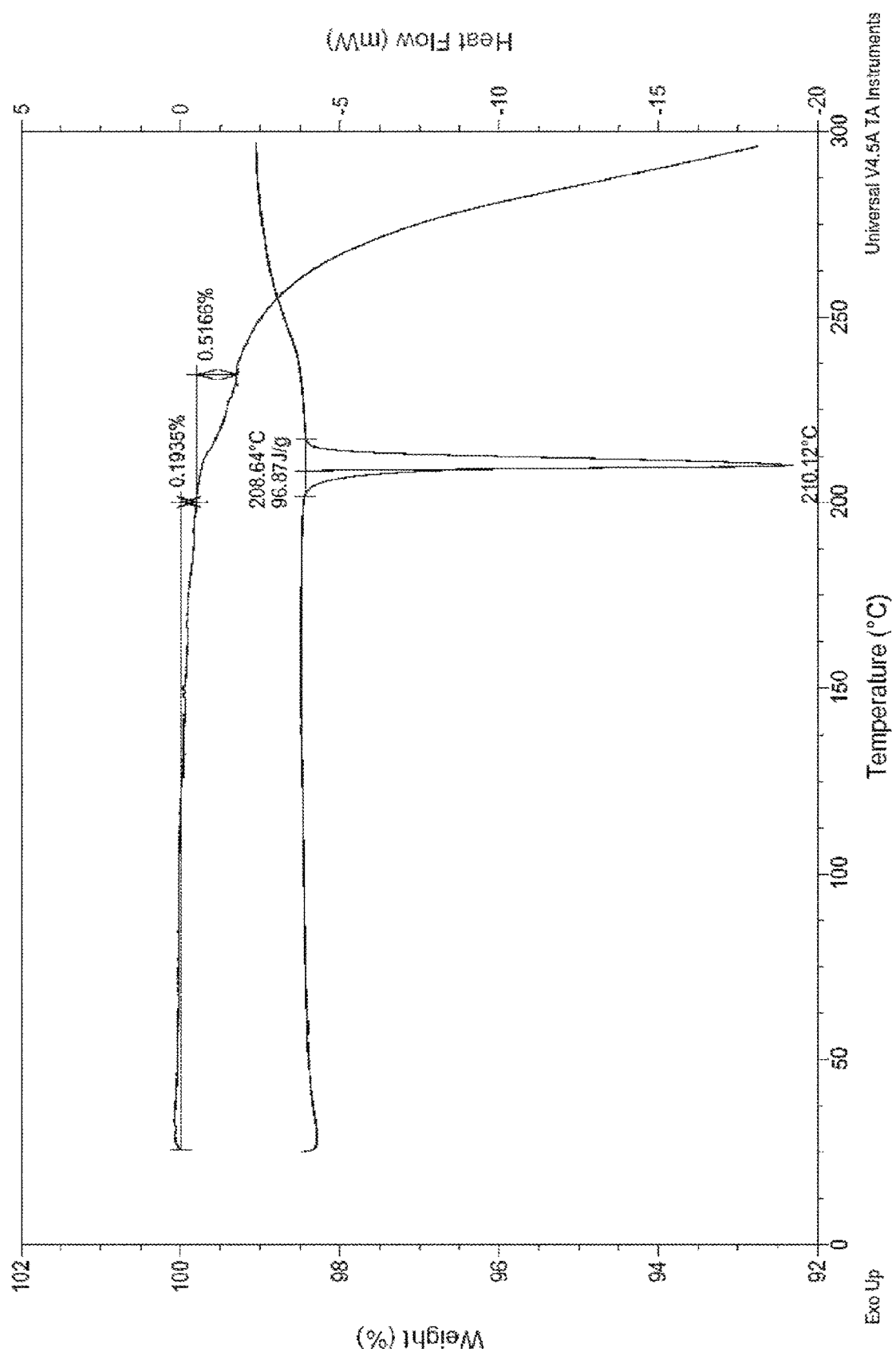
FIG. 2B shows a representative thermogravimetric analysis (TGA) and differential scanning calorimetry (DSC) analysis of crystalline form I of Compound 5.

As used herein, Form I of Compound 5 refers to a crystalline form of Compound 5 which can be characterized by an XRPD pattern substantially the same as FIG. 2A; an XRPD spectrum having the major peaks (e.g., peaks with relative intensity of 20% or above, 30% or above, 40% or above, 50% or above, 60% or above, 70% or above, 80% or above, or 90% or above) of FIG. 2A; an XRPD spectrum having one or more (e.g., 1, 2, 3, 4, 5, 6, 7, 8, 9, 10, 11, 12, 13, 14, 15, 16, 17, 18, 19, 20, 21, 22, 23) of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, 0.2°; a DSC pattern having an endotherm peak with peak temperature at about 210.1° C.; a DSC profile substantially the same as shown in FIG. 2B; a TGA profile substantially the same as shown in FIG. 2B; or a combination thereof. Major peaks of an XRPD spectrum as used herein refer to peaks having diffraction angles between 4-30 degrees (2 theta) and a relative intensity of 10% or above. In some embodiments, major peaks of an XRPD spectrum can refer to peaks with a relative intensity of 20% or above, 30% or above, 40% or above, 50% or above, 60% or above, 70% or above, 80% or above, or 90% or above. Some details of form I of Compound 5 are also described in U.S. Provisional Appl. No. 62/678,634, filed May 31, 2018, the priority of which is claimed in this application, and the content of which is incorporated by reference in its entirety.

For example, in some embodiments, the crystalline form I of Compound 5 is characterized by an XRPD spectrum having four or more of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°. In some embodiments, the crystalline form I of Compound 5 is characterized by an XRPD spectrum having eight or more of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, 0.2°. In some embodiments, the crystalline form I of Compound 5 is characterized by an XRPD spectrum having twelve or more of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°. In some embodiments, the crystalline form I of Compound 5 is characterized by an XRPD spectrum having sixteen or more of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°. In some embodiments, the crystalline form I of Compound 5 is characterized by an XRPD spectrum having all of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°. In some embodiments, the crystalline form I of Compound 5 is characterized by an XRPD spectrum substantially the same as shown in FIG. 2A. In some embodiments, the crystalline form I of Compound 5 can be further characterized by a DSC pattern having an endotherm peak with peak temperature at about 210.1° C. and/or a DSC profile substantially the same as shown in FIG. 2B. In some embodiments, the crystalline form I of Compound 5 can be further characterized by a TGA profile substantially the same as shown in FIG. 2B.

The size of the crystals used for preparing tablets or capsules comprising compounds of the present invention can be of significance. If the crystals are too small, they may stick to the plunger in the tablet machines or otherwise have an undesired flow property. On the other hand, they cannot be too large either. The dissolution rate in the intestines decreases when crystal size increases. Hence, if the crystals are too large it may compromise the bioavailability of the compounds. Particle size distribution may be described using quantiles, e.g. D10%, D50%, and D90% etc. For brevity, the "%" sign may be omitted in this application. Thus, D10 means the same as D10%. As used herein, "particle size distribution" means the cumulative volume size distribution of equivalent spherical diameters as determined by Malvern Mastersizer 3000 Particle Size Analyzer.

In some embodiments, the crystals of Form I of Compound 5 can be characterized by a particle size distribution of 1) D90: about 150 um to about 250 um; D50: about 90 um to about 140 um; and D10 of about 40 um to about 75 um; 2) D90: about 100 um to about 150 um; D50: about 20 um to about 60 um; and D10 of about 5 um to about 15 um; 3) D90: about 120 um to about 200 um; D50: about 50 um to about 100 um; and D10 of about 10 um to about 20 um; 4) D90: about 140 um to about 180 um; D50: about 90 um to about 130 um; and D10 of about 55 um to about 85 um; 5) D90: about 50 um to about 100 um; D50: about 20 um to about 30 um; and D10 of about 3.5 um to about 9 um; 6) D90: about 70 um to about 95 um; D50: about 25 um to about 40 um; and D10 of about 5 um to about 15 um; 7) D90: about 120 um to about 160 um; D50: about 55 um to about 85 um; and D10 of about 5 um to about 15 um; or 8) D90: about 90 um to about 130 um; D50: about 35 um to about 60 um; and D10 of about 10 um to about 15 um. In some embodiments, the crystals of Form I of Compound 5 can be characterized by a particle size distribution of D90: about 80 um to about 120 um; and D50: about 30 um to about 60 um. The unit "um" herein refers to micrometer.

The particle size distribution herein can be adjusted by the crystallization conditions. For example, as detailed in the Examples section, the inventors have found that a step-wise slow cooling in the presence of seed crystals can help to achieve a desired particle size distribution. Typically, following this step-wise cooling procedure, the crystallization process described herein can produce crystalline Form I with a narrower particle size distribution, which is beneficial for further formulation processing. The seed crystals can be prepared by the process described herein without the step of adding the seed crystals. In some embodiments, the seed crystals used in the step-wise cooling procedure can be sieved to obtain a desired particle size distribution of the seed crystals themselves. For example, in some embodiments, the seed crystals can be prepared by passing bulk crystals through a 200-mesh sieve and collecting the crystals that remain as the seed crystals, i.e., those do not pass through the sieve. In some embodiments, the seed crystals can be used without a sieving procedure. In some embodiments, other sizes of sieve can be used to obtain a different particle size distribution of the seed crystals. In some embodiments, the particle size distribution can be adjusted by milling, such as wet milling as described herein.

In any of the embodiments described herein, the substantially pure Compound 5 can consist essentially of Form I of Compound 5. In any of the embodiments described herein, Compound 5 can exist in Form I. In any of the embodiments described herein, Compound 5 can also exist as an amorphous form. In any of the embodiments described herein, the substantially pure Compound 5 or a pharmaceutical composition comprising Compound 5 can include Compound 5 solely in the form of Form T, i.e., with no other solid form of Compound 5 identifiable by XRPD. In any of the embodiments described herein, the substantially pure Compound 5 or a pharmaceutical composition comprising Compound 5 can also include Compound 5 in a mixture of Form I and amorphous form. In some embodiments, the substantially pure Compound 5 or a pharmaceutical composition comprising Compound 5 can include Compound 5 in an amorphous form.

Exemplary methods for preparing crystalline Compound 5 are described herein. Typically, a substantially pure Compound 4 is dissolved in a solvent (e.g., ethanol and ethyl acetate mixture) to form a solution; less than about 1 equivalent (e.g., 0.95 equivalent) of methane sulfonic acid can be added to the solution to form Compound 5. The addition of methane sulfonic acid can be carried out, for example, at elevated temperature such as about 50-80° C., such as about 55-65° C. In some embodiments, Compound 5 can be precipitated out after addition of the methane sulfonic acid, e.g., after addition of the majority of the methane sulfonic acid. In some embodiments, Compound 5 can be precipitated, for example, through cooling the solution or reducing the amount of the solvent by evaporation, or adding an antisolvent. In some embodiments, a seed crystal of Form I can be added to facilitate/control the crystallization process. An example of preparation of Form I of Compound 5 is provided in the Examples section.

In some embodiments, Compound 5 can be recrystallized under suitable conditions. Suitable solvents for recrystallization include, but are not limited to, THF, toluene, MeOH, ethanol, n-propanol, isopropanol, isobutanol, methyl tert-butyl ether, ethyl ether, isoamylol, isopentanol, butyl acetate, ethyl formate, 1,4-dioxane, n-butanol, tert-butanol, n-heptane, cyclohexane, dicloromethane, methyl isobutyl ketone, dimethylbenzene, isobutyl acetate, 2-butanone, acetonitrile, acetone, ethyl acetate, isopropyl acetate, and water. The solvents can be used alone or in various combinations. Recrystallization technics are generally known in the art.

Method of Preparation

U.S. Publication No. 2017/0355696 A1 describes a method of preparing Compound 4 and various pharmaceutically acceptable salts thereof. The exemplified synthetic process in U.S. Publication No. 2017/0355696 A1 includes a two-step conversion from the aniline compound, corresponding to Compound 1 of this disclosure, into the bismesylate of Compound 4, which has a low yield.

As shown herein, representative methods of preparation of Compound 4, or a pharmaceutically acceptable salt, (or alternatively referred to as synthetic methods), can provide the desired Compound 4, or a pharmaceutically acceptable salt, in improved yield and high purity and can be adapted for large-scale manufacture.

In various embodiments, the present invention provides a novel method of preparing Compound 4, or a pharmaceutically acceptable salt thereof. The method typically includes converting a compound of Formula III, or a salt thereof, into compound 4, typically under an elimination reaction condition:

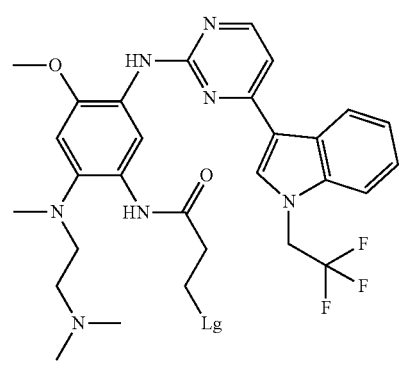

Formula III wherein Lg in Formula III is a leaving group, such as a halide (e.g., Cl).

In some embodiments, compounds of Formula III can be prepared from Compound 1 or a salt thereof. Accordingly, in some embodiments, the method comprises 1) converting Compound 1, or a salt thereof, into a compound of Formula III, or a salt thereof, for example, under an amide formation condition, wherein Lg in Formula III is a leaving group;

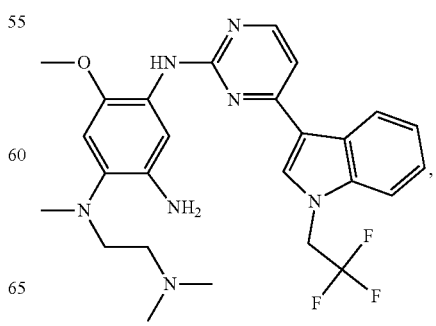

1

Formula III and 2) converting the compound of Formula III, or a salt thereof, into compound 4, for example, under an elimination reaction condition.

While the prior method of synthesizing Compound 4 from Compound 1 can be achieved by a one-step reaction with an acryl chloride or acryl anhydride, it was found that the two-step conversion through an intermediate compound of Formula III provides significant advantages. For example, by using this two-step conversion method, the final yield of Compound 4 or a pharmaceutically acceptable salt can be improved. The purification of Compound 4 or a pharmaceutically acceptable salt can also be simplified, which makes the synthetic route of the present disclosure more suitable for large scale manufacturing. Typically, Compound 1 or a salt thereof can react with an acid of Formula IV-Acid,

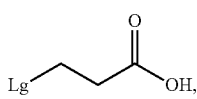

or an activated form thereof, such as an acyl chloride of Formula IV,

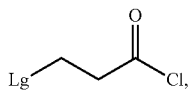

wherein Lg is a leaving group, to form a compound of Formula III under an amide formation condition. Amide formations are well known in the art and various conditions can be adapted for the synthetic methods herein. For example, in some embodiments, Compound 1 can be mixed with an acyl chloride of Formula IV in a suitable solvent (e.g., an ether solvent, such as THF, which can be mixed with water, such as in about 10:1 ratio). Typically, the reaction can be carried out at a temperature below room temperature, such as around 0-10° C.; external base is typically not required. Exemplary conditions are shown in the Examples section. The Lg in Formula IV-Acid or Formula IV is typically the same as the Lg in Formula III. For example, typically, the Lg in Formula III, Formula TV-Acid or Formula IV can all be a leaving group selected from a halide and an oxygen containing leaving group, such as —O—SO$_2$—R, wherein R is an alkyl (e.g., methyl, CF$_3$) or an aryl (e.g., phenyl, p-tolyl, etc.). In some specific embodiments, the Lg in Formula III, Formula IV-Acid or Formula IV can be Cl. However, in some embodiments, the Lg in Formula IV-Acid or Formula IV can also be different from, and can be converted into, the Lg in Formula III.

In some embodiments, the compound of Formula III is not isolated before proceeding to the next step. In some embodiments, the compound of Formula III can also be isolated and then used in the next step.

The compound of Formula III is also a novel composition of the present disclosure. In some embodiments, the present disclosure also provides a compound of Formula III, or a salt thereof (e.g., a pharmaceutically acceptable salt thereof), Formula III wherein Lg is a leaving group (e.g., as defined herein). In some embodiments, Lg is a halide such as Cl. In some embodiments, Lg is an oxygen containing leaving group as described herein. In some embodiments, Lg can also be OH, or a protected OH. In some embodiments, Lg can also be an alkoxy, such as a $C_{1-6}$ alkoxy (e.g., methoxy, ethoxy, isopropoxy, and etc.). In some embodiments, the present disclosure also provides a composition comprising Compound 4, or a pharmaceutically acceptable salt thereof, and a compound of Formula III (e.g., described herein, e.g., with Lg being Cl or OH, etc.), or a salt thereof. In some embodiments, the composition is substantially free of the compound of Formula III or a salt thereof, e.g., less than 1%, less than 0.5%, less than 0.2%, less than 0.1% as measured by HPLC (e.g., the HPLC method described in Example 1, e.g., using 220 nm as the detection wavelength). In some embodiments, the composition is a pharmaceutical composition, which in some embodiments, comprises a therapeutically effective amount of Compound 4 or a pharmaceutically acceptable salt thereof, e.g., the mesylate salt Compound 5.

The Compound of Formula III can typically be converted into Compound 4 through treatment with a base, for example, an alkali base such as an alkali hydroxide, e.g., NaOH, KOH, etc. In some specific embodiments, the conversion of Compound of Formula III into Compound 4 can comprise contacting the compound of Formula III with KOH. Typically, the elimination reaction can be carried out in the same solvent used for the amide formation described above, e.g., using a mixture of THF and water (e.g., in a ratio of 10:1). The amount of base can be adjusted, which is typically in excess, such as 2-5 equivalents. The elimination reaction can be carried out under heat. In some embodiments, other elimination conditions can also be used to effect the conversion. Elimination reactions of a leaving group from a beta-position of an amide are well known and can be adapted for the synthetic methods herein.

Exemplary conditions of converting Compound 1 into Compound 4 are shown in the Examples section. As described, the overall yield of Compound 4 from Compound 1 is much improved and is over 70%. Thus, the synthetic methods herein, among other advantages, at least greatly facilitate large-scale manufacturing of Compound 4.

In some embodiments, the method further comprises purifying Compound 4 through recrystallization, e.g., in a mixture of isopropanol and water. In some embodiments, the recrystallization can further improve the purity of Compound 4. For example, as explained herein, in some embodiments, a recrystallization in a mixture of isopropanol and water can reduce the amount of impurity A and B (as defined herein). Exemplary conditions are shown in the examples.

In some embodiments, a pharmaceutically acceptable salt of Compound 4 is desired. In such embodiments, the method further comprises a step of reacting Compound 4 with a suitable acid to form the pharmaceutically acceptable salt of Compound 4. In some embodiments, Compound 4 can be prepared in high purity through the processes described herein, which when used as a starting material, can also provide a pharmaceutically acceptable salt with a high purity. Thus, in some embodiments, the present disclosure also provides a method of preparing a pharmaceutically acceptable salt from reacting a substantially pure Compound 4 (e.g., described herein) with a suitable acid (e.g., any of those described herein, such as HCl, methanesulfonic acid, etc.). In some embodiments, the substantially pure Compound 4 has a purity by HPLC of at least 95% (e.g., about 96%, about 97%, about 98%, about 98.5%, about 99%, or above 99%). In some embodiments, the substantially pure Compound 4 can be substantially free of an impurity characterized by an HPLC relative retention time of about 1.02 (impurity A). For example, in some embodiments, the impurity A can be present in less than 1%, less than 0.8%, less than 0.5%, less than 0.2%, less than 0.1% as measured by HPLC. In some embodiments, the impurity A is not detected (or below the detection limit) by HPLC. In some embodiments, the substantially pure Compound 4 can be substantially free of an impurity characterized by an HPLC relative retention time of about 0.88 (impurity B). For example, in some embodiments, the impurity B can be present in less than 0.5%, less than 0.2%, or less than 0.1% as measured by HPLC. In some embodiments, the impurity B is not detected (or below the detection limit) by HPLC. In some embodiments, the substantially pure Compound 4 can be substantially free of both impurity A and impurity B, e.g., the combined amount of impurity A and B is less than 0.5%, less than 0.2%, or less than 0.1% as measured by HPLC. In some embodiments, the impurity A and B are both not detected (or below the detection limit) by HPLC. In some embodiments, the term "as measure by HPLC" refers to using the HPLC method as shown in Example 1, e.g., using 220 nm as the detection wavelength. The pharmaceutically acceptable salt prepared by the method herein typically can have a purity by HPLC of greater than about 90% (e.g., about 95%, about 97%, about 98%, about 99%, or any ranges between the specified values).

In some embodiments, the substantially pure Compound 4 is converted into its monomesylate salt Compound 5. In some embodiments, Compound 5 is also substantially pure. For example, in some embodiments, Compound 5 is characterized by a purity by weight and/or by HPLC area of least 70% (e.g., at least 75%, at least 80%, at least 85%, at least 90%, at least 95%, at least 97%, or at least 99%). In some embodiments, the substantially pure Compound 5 has a purity by HPLC of at least 95% (e.g., about 96%, about 97%, about 98%, about 98.5%, about 99%, or above 99%). In some embodiments, the substantially pure Compound 5 can be substantially free of impurity A (as defined herein). For example, in some embodiments, the impurity A can be present in less than 1%, less than 0.8%, less than 0.5%, less than 0.2%, less than 0.1% as measured by HPLC. In some embodiments, the impurity A is not detected (or below the detection limit) by HPLC. In some embodiments, the substantially pure Compound 5 can be substantially free of impurity B (as defined herein). For example, in some embodiments, the impurity B can be present in less than 0.5%, less than 0.2%, or less than 0.1% as measured by HPLC. In some embodiments, the impurity B is not detected (or below the detection limit) by HPLC. In some embodiments, the substantially pure Compound 5 can be substantially free of both impurity A and impurity B, e.g., the combined amount of impurity A and B is less than 0.5%, less than 0.2%, or less than 0.1% as measured by HPLC. In some embodiments, the impurity A and B are both not detected (or below the detection limit) by HPLC. In some embodiments, the term "as measure by HPLC" refers to using the HPLC method as shown in Example 1, e.g., using 220 nm as the detection wavelength.

Compound 1 can be prepared by various methods. In some embodiments, Compound 1 for the synthetic methods described herein can be prepared by a process comprising reducing compound A9 or a salt thereof with $H_2$ in an ether solvent (e.g., tetrahydrofuran, tert-butyl methyl ether, etc.) in the presence of a catalyst (e.g., a heterogeneous catalyst such as Pd/C):

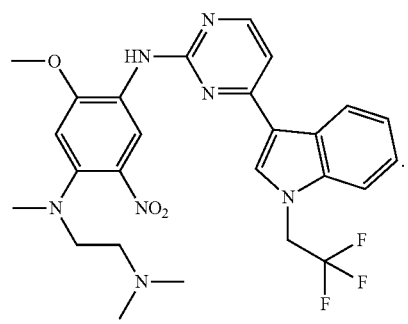

A9

It was unexpectedly found that reducing the nitro group of A9 with $H_2$ can be more effectively carried out in an ether solvent such as tetrahydrofuran (THF), rather than a more commonly used alcoholic solvent such as ethanol. For example, the hydrogenation reaction can proceed to completion (or near completion) in a shorter period of time, with an improved yield. Various hydrogenation reaction conditions can be used. For example, various catalysts for hydrogenation such as heterogeneous catalysts are suitable and can be selected by those skilled in the art in view of the present disclosure. Other ether solvents similar to THF can also be used. The pressure of $H_2$, as well as reaction temperature, concentration of compound A9 in the solvent can be adjusted by those skilled in the art in view of the present disclosure. An exemplary hydrogenation condition is shown in the Examples section. Compound 1 prepared by the methods herein can also have a high purity, e.g., a purity by HPLC of at least 85% (e.g., about 90%, about 95%, about 96%, about 97%, about 98%, about 98.5%, about 99%, or above 99%). In some embodiments, Compound 1 can also be in a crystalline form, for example, in some embodiments, Compound 1 can be recrystallized from a suitable solvent, such as ethyl acetate, etc. In some embodiments, a crystalline Compound 1 can be used as a starting material for reacting with an acid of Formula IV-Acid, or an activated form thereof, such as an acyl chloride of Formula IV, to form a compound of Formula III under an amide formation condition.

Compound A9 can be prepared via various methods. In some embodiments, Compound A9 for the synthetic methods described herein can be prepared by a process comprising reacting compound A7 with compound A8, or a salt thereof, in a solvent (e.g., CH₃CN) in the presence of a base (e.g., a carbonate base, such as K₂CO₃):

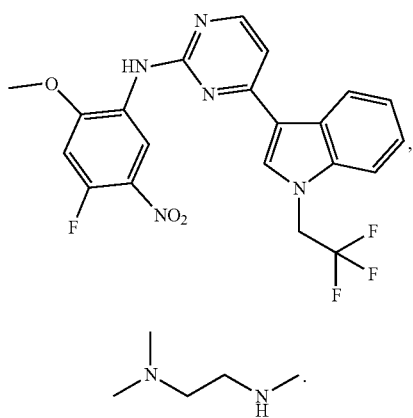

A7

A8

Various reaction conditions can be used. For example, various base and its amounts can be chosen by those skilled in the art in view of the present disclosure. Typically, it was found that a carbonate base such as K₂CO₃ in the amount of less than 3 equivalents, e.g., about 1.2 equivalents, can lead to improved yields. Solvent such as CH₃CN can be used for this transformation. The reaction temperature, concentration of compound A7 in the solvent etc. can be adjusted by those skilled in the art in view of the present disclosure. An exemplary reaction condition is shown in the Examples section.

Compound A7 can also be prepared by various suitable methods. In some embodiments, Compound A7 for the synthetic methods described herein can be prepared by a process comprising reacting compound A5 with compound A6, or a salt thereof, in a solvent (e.g., isopropanol) in the presence of a catalytic acid (e.g., para-toluenesulfonic acid (PTSA)):

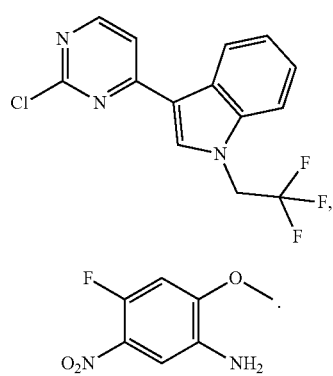

A5

A6

Various reaction conditions for similar displacement reactions are known in the art and can be adapted for the methods herein. It was found that only a catalytic amount of acid is needed for this reaction. For example, as shown in the examples section, as low as 0.2 equivalent of PTSA was used in the reaction of Compounds A5 and A6 to afford Compound A7. Typically, Compound A7 produced as an HCl salt, which can be optionally neutralized prior to the next step, e.g., prior to reaction with Compound A8. Solvent such as isopropanol can be used for this transformation. The reaction temperature, concentration of compound A5 in the solvent etc. can be adjusted by those skilled in the art in view of the present disclosure. An exemplary reaction condition is shown in the Examples section.

Compound A5 can also be prepared by various methods. In some embodiments, Compound A5 for the synthetic methods described herein can be prepared by a process comprising reacting compound A3 with compound A4, in a solvent (e.g., N,N-dimethyl acetamide (DMAc)) in the presence of a base (e.g., a carbonate base, such as K₂CO₃):

A3

A4

It was found that the use of a weak base such as a carbonate base is sufficient for this transformation and more advantageous. For example, an earlier method used for this transformation employs a strong base such as NaH, which limits its applicability in large scale preparations. In this disclosure, it was found that using a carbonate base, such as K₂CO₃, led to similar yields with using NaH. Thus, the reaction of A3 and A4 to provide A5 can be advantageously carried out with a carbonate base, which is much easier for a large scale synthesis compared to prior methods. The solvent for this transformation with a carbonate base can typically be an aprotic polar solvent, such as DMAc. The reaction temperature, concentration of compound A3 in the solvent etc. can be adjusted by those skilled in the art in view of the present disclosure. An exemplary reaction condition is shown in the Examples section.

Compound A3 can also be prepared by various methods. In some embodiments, Compound A3 for the synthetic methods described herein can be prepared by a process comprising reacting compound A1 with indole, in a solvent (e.g., 2-methyl tetrahydrofuran (2-MeTHF)) in the presence of a base (e.g., MeMgBr):

A1

It was found that Lewis acid catalyzed Friedel-Crafts reaction of A1 with indole does not work as well. Rather, the reaction proceeds smoothly in high yield if a base is used, such as MeMgBr, typically in excess of 1 equivalent, such as about 2 equivalents. The solvent for this transformation can typically be an ether solvent, such as 2-MeTHF. The reaction temperature, concentration of compound A1 in the solvent etc. can be adjusted by those skilled in the art in view of the present disclosure. An exemplary reaction condition is shown in the Examples section.

In some embodiments, the method for preparing Compound 4, or a pharmaceutically acceptable salt thereof, can comprise a reaction scheme according to the following:

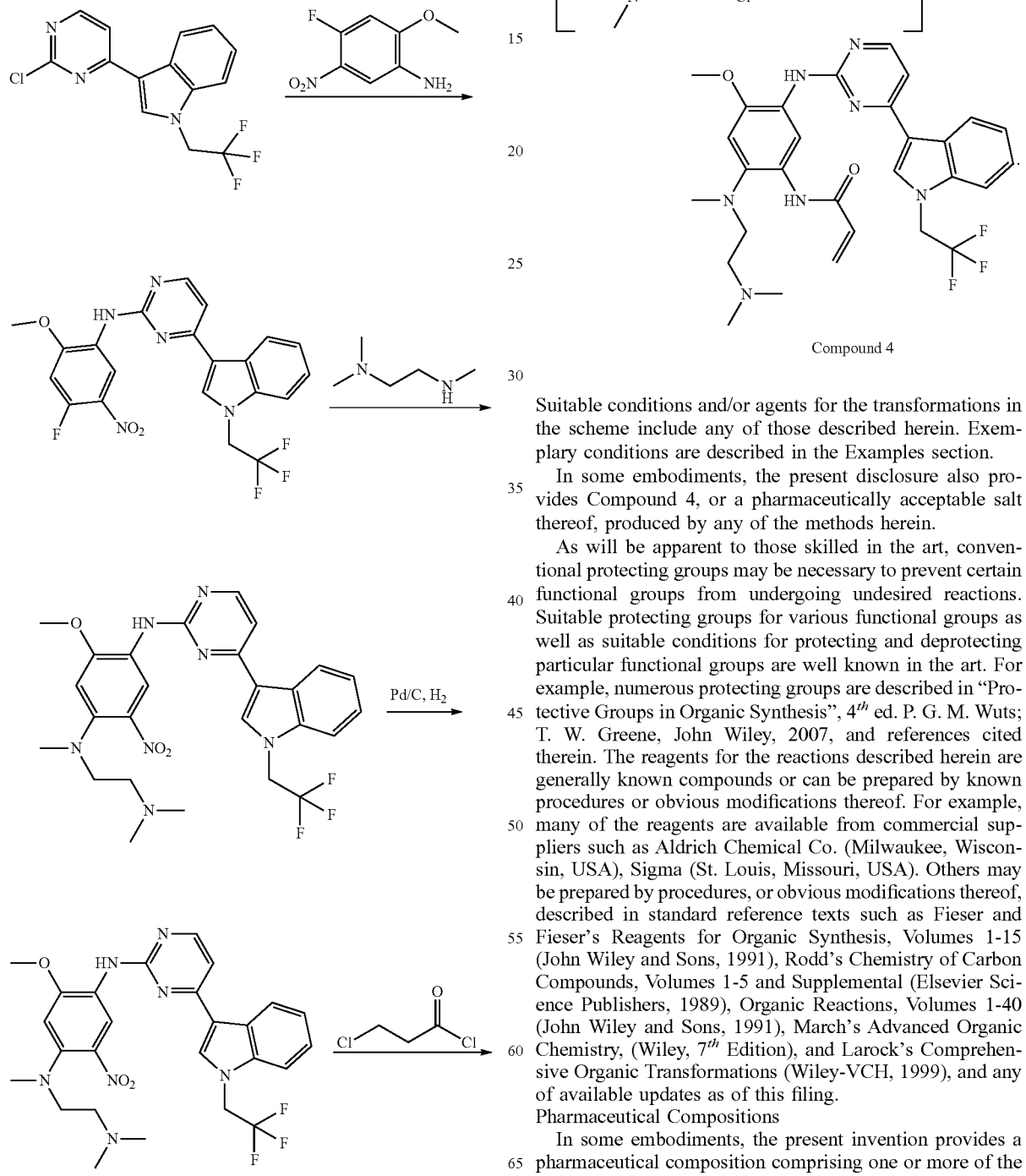

Compound 4

Suitable conditions and/or agents for the transformations in the scheme include any of those described herein. Exemplary conditions are described in the Examples section.

In some embodiments, the present disclosure also provides Compound 4, or a pharmaceutically acceptable salt thereof, produced by any of the methods herein.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", $4^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wisconsin, USA), Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, $7^{th}$ Edition), and Larock's Comprehensive Organic Transformations (Wiley-VCH, 1999), and any of available updates as of this filing.

Pharmaceutical Compositions

In some embodiments, the present invention provides a pharmaceutical composition comprising one or more of the compounds described herein (e.g., substantially pure Compound 4 or a pharmaceutically acceptable salt thereof, e.g., Compound 5). Typically, the pharmaceutical composition comprises a therapeutically effective amount of one or more of the compounds described herein (e.g., substantially pure Compound 4 or a pharmaceutically acceptable salt thereof, e.g., Compound 5) and optionally a pharmaceutically acceptable excipient or carrier. In some embodiments, the pharmaceutical composition comprises the substantially pure Compound 4, or a pharmaceutically acceptable salt thereof, e.g., as described herein. In some embodiments, the pharmaceutical composition comprises the Compound 4, or a pharmaceutically acceptable salt thereof, produced by any of the synthetic methods herein. In some embodiments, the pharmaceutical composition comprises the substantially pure Compound 5 as described herein. In some embodiments, the pharmaceutical composition comprises Compound 5 in Form I and/or amorphous form. The pharmaceutical composition can be formulated for any routes of administration, for example, oral administration.

Certain specific embodiments of the present invention are directed to a pharmaceutical composition comprising a therapeutically effective amount of substantially pure Compound 4, or a pharmaceutically acceptable salt thereof, e.g., as described herein, and optionally a pharmaceutically acceptable excipient or carrier. In some embodiments, the pharmaceutical composition comprising the substantially pure Compound 4, or a pharmaceutically acceptable salt thereof, e.g., as described herein, can be formulated for oral, parenteral, nasal, pulmonary, buccal, topical or transdermal administration. In some embodiments, the pharmaceutical composition comprising the substantially pure Compound 4, or a pharmaceutically acceptable salt thereof, e.g., as described herein, can be formulated as a solid dosage form. In some embodiments, the solid dosage form is an oral solid dosage form. In some embodiments, the solid dosage form is a capsule or tablet. In some embodiments, the solid dosage form is enteric coated. However, in some embodiments, the solid dosage form is not enteric coated.

Certain specific embodiments of the present invention are directed to a pharmaceutical composition comprising a therapeutically effective amount of Compound 5 and optionally a pharmaceutically acceptable excipient or carrier. In some embodiments, the pharmaceutical composition comprising Compound 5 can be formulated for oral, parenteral, nasal, pulmonary, buccal, topical or transdermal administration. In some embodiments, the pharmaceutical composition comprising Compound 5 can be formulated as a solid dosage form. In some embodiments, the solid dosage form is an oral solid dosage form. In some embodiments, the solid dosage form is a capsule or tablet. In some embodiments, the solid dosage form is enteric coated. However, in some embodiments, the solid dosage form is not enteric coated. In some embodiments, the pharmaceutical composition comprises the substantially pure Compound 5 as described herein. In some embodiments, the Compound 5 exists in Form I. In some embodiments, the pharmaceutical composition is free or substantially free of Compound 5 in any solid form other than Form I. For example, in some embodiments, there is no detectable solid form of Compound 5 other than Form I in the pharmaceutical composition. In some embodiments, Form I of Compound 5 in the pharmaceutical composition is characterized by a particle size distribution, e.g., any of those described herein. For example, in some embodiments, Form I of Compound 5 in the pharmaceutical composition can be characterized by a particle size distribution of D90: about 80 um to about 120 um; and D50: about 30 um to about 60 um. Other suitable particle size distributions of Form I of Compound 5 are described herein. In some embodiments, the pharmaceutical composition comprises Compound 5 in a mixture of Form I and amorphous form.

The pharmaceutical composition comprising Compound 5 is typically storage stable. For example, in one example, when tested for stability by storing at 40° C. at a relative humidity of 75% for up to 6 months, the pharmaceutical composition contains substantially the same amount of Compound 5 as determined by HPLC, with similar levels of (e.g., no increased amount of) impurities or degradants as determined by HPLC, and has essentially the same dissolution profile as determined by the dissolution methods described herein. Typically, the solid dosage form herein can be formulated as an immediate release formulation, for example, releasing at least 70% (e.g., at least 80%, at least 85%, at least 90%, or essentially all) of the Compound 5 within 30 minutes, when tested using Chinese Pharmacopeia 2015 Edition, General Rule 4, 0931, Method 2, at a paddle speed of 50 rpm.

The pharmaceutical composition herein can include Compound 5 in various amounts, for example, in an amount effective for treating the diseases or disorders described herein, such as cancer (e.g., non-small cell lung cancer). In some embodiments, the active ingredient in the pharmaceutical composition can consist essentially of or consist of Compound 5. Typically, Compound 5 can be included in an amount of about 5% to about 25% by weight of the pharmaceutical composition.

In a typical dosage form, a pharmaceutically acceptable salt of Compound 4 (e.g., described herein) can be used as active pharmaceutical ingredient (API). However, in some embodiments, the APT of a dosage form can include Compound 4 (e.g., described herein) as a free base. In some embodiments, the API can include two or more different pharmaceutically acceptable salts of Compound 4 (e.g., described herein). In some embodiments, the API can include Compound 4 (e.g., described herein) as a free base in a mixture with one or more pharmaceutically acceptable salts of Compound 4 (e.g., described herein).

Various excipients or carriers can be included in the pharmaceutical compositions described herein. Typically, the pharmaceutical composition herein can include one or more excipients or carriers selected from filling agents (such as lactose, microcrystalline cellulose, mannitol, etc.), disintegrants (e.g., croscarmellose sodium), glidants (e.g., colloidal silicon dioxide), lubricants (e.g., sodium stearyl fumarate), antioxidants, stabilizers, preservatives, diluents, solvents, sweetening agents, viscosity-increasing agents, chelating agents, colorants, surfactants, flavorings, coating agents, gelling agents, binders and release modifiers. Those skilled in the art would know that other excipients/carriers can also be used and know how to choose appropriate excipients/carriers when formulating the compounds herein according to the intended uses. In some specific embodiments, the pharmaceutical composition includes one or more (e.g., 1, 2, 3, 4, 5, or 6) of the following: lactose, microcrystalline cellulose, mannitol, croscarmellose sodium, colloidal silicon dioxide, and sodium stearyl fumarate. Any suitable amount of such excipients and carriers can be used. The amount of excipients and/or carriers can also be adjusted, for example, to achieve a desired immediate release dissolution profile described herein. In some embodiments, the excipients and carriers are used in an amount at or below the upper limit of the respective excipient or carrier that the U.S. Food and Drug Administration, or other corresponding competent agencies, has determined to be safe for human use. Additional suitable examples of excipients or carriers can be found in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), the contents of which are incorporated herein by reference in their entirety.

Methods of Treatment

The compounds and pharmaceutical compositions described herein can be used for treating various diseases and disorders. As described in US Publication No. 2017/0355696 A1, Compound 4 and its pharmaceutically acceptable salt can be a potent and selective inhibitor against EGFR variant(s) or mutant(s), e.g., activated or resistant mutant form of EGFR, for example, a L858R mutant, an Exon19 deletion mutant and/or a T790M mutant.

In some embodiments, a method of treating a disease or disorder in a subject in need thereof is provided. In some embodiments, the method comprises administering to the subject the substantially pure Compound 4, or a pharmaceutically acceptable salt thereof, e.g., as described herein. In some embodiments, the method comprises administering to the subject the Compound 4, or a pharmaceutically acceptable salt thereof, produced by any of the synthetic methods herein. In some embodiments, the method comprises administering Compound 5 to the subject. In some embodiments, the disease or disorder is mediated by EGFR (e.g., activated or resistant mutant form of EGFR). In some embodiments, the disease or disorder is mediated by L858R mutant, Exon19 deletion mutant and/or T790M mutant. In some embodiments, the disease or disorder can be, but is not limited to, ovarian cancer, cervical cancer, colorectal cancer (e.g., colon adenocarcinoma), breast cancer, pancreatic cancer, glioma, glioblastoma, melanoma, prostate cancer, leukemia, lymphoma, non-Hodgkin's lymphoma, gastric cancer, lung cancer (e.g., non-small cell lung cancer), hepatocellular carcinoma, gastrointestinal stromal tumors (GIST), thyroid cancer, cholangiocarcinoma, endometrial cancer, renal carcinoma, anaplastic large cell lymphoma, acute myeloid leukemia (AML), multiple myeloma and/or mesothelioma.

In some embodiments, the method is for treating cancer. In some embodiments, the method is for treating ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular carcinoma, gastrointestinal stromal tumor, thyroid cancer, cholangiocarcinoma, endometrial cancer, kidney cancer, anaplastic large cell lymphoma, acute myeloid leukemia, multiple myeloma, mesothelioma, or any combination thereof. In some embodiments, the method is for treating lung cancer. In some embodiments, the lung cancer is non-small cell lung cancer.

In any of the methods described herein, the subject can be resistant to one or more EGFR inhibitors other than Compound 4 or a pharmaceutically acceptable salt thereof (e.g., Compound 5). In some embodiments, the subject can be resistant to one or more EGFR inhibitors chosen from gefitinib, erlotinib, and icotinib. In some embodiments, the subject can experience side-effects with wild-type EGFR inhibition.

Typically, the methods described herein include administering to the subject a therapeutically effective amount of Compound 4, or a pharmaceutically acceptable salt thereof, e.g., Compound 5, or the pharmaceutical compositions described herein. In some embodiments, the method comprises administering to the subject a therapeutically effective amount of a pharmaceutical composition comprising the substantially pure Compound 4, or a pharmaceutically acceptable salt thereof, e.g., as described herein. In some embodiments, the method comprises administering to the subject a therapeutically effective amount of a pharmaceutical composition comprising the Compound 4, or a pharmaceutically acceptable salt thereof, produced by any of the synthetic methods herein. The compounds and pharmaceutical compositions can be administered to the subject via any routes of administration. For example, in some embodiments, the compounds and pharmaceutical compositions can be administered to the subject orally. In some specific embodiments, the method comprises orally administering to the subject a therapeutically effective amount of Compound 5.

In any of the embodiments described herein, Compound 4, such as the substantially pure Compound 4, or a pharmaceutically acceptable salt thereof, e.g., Compound 5, can be used in a monotherapy. For example, in some embodiments, the active agent for the methods or pharmaceutical compositions herein can consist or consist essentially of Compound 4 or a pharmaceutically acceptable salt thereof, e.g., the substantially pure Compound 4, or a pharmaceutically acceptable salt thereof, e.g., Compound 5, which can be in Form I, amorphous form, or a combination thereof. The methods described herein can also be used in combination with other therapies. For example, the methods herein can be used in combination with one or more selected from a surgical procedure (e.g., conventional anticancer surgical therapy), radiotherapy, chemotherapy and antitumor immunotherapy.

In some embodiments, the method can include administering, e.g., orally, to the subject a therapeutically effective amount of a pharmaceutical composition comprising the substantially pure Compound 4, or a pharmaceutically acceptable salt thereof, e.g., as described herein, in parallel, concurrently, sequentially, or separately with a chemotherapy or antitumor immunotherapy. In some embodiments, the method can include administering, e.g., orally, to the subject a therapeutically effective amount of a pharmaceutical composition comprising the Compound 4, or a pharmaceutically acceptable salt thereof, produced by any of the synthetic methods herein, e.g., as described herein, in parallel, concurrently, sequentially, or separately with a chemotherapy or antitumor immunotherapy. In some embodiments, the method can include administering, e.g., orally, to the subject a therapeutically effective amount of Compound 5 in parallel, concurrently, sequentially, or separately with a chemotherapy or antitumor immunotherapy. The chemotherapy or immunotherapy includes, but is not limited to, one or more of the following types of antitumor agents: alkylating agent (e.g., carboplatin, oxaliplatin, cisplatin, cyclophosphamide, nitrosourea, nitrogen mustard, melphalan), antimetabolite (e.g. gemcitabine), and anti-folic acid agent (e.g., 5-fluorouracil and tegafur, raltitrexed, methotrexate, cytarabine, hydroxyurea), topoisomerase inhibitor (e.g., etoposide, topotecan, camptothecin), anti-mitotic agent (e.g., vincristine, vinblastine, vinorelbine, paclitaxel, taxotere), anti-tumor antibiotic (e.g., doxorubicin, bleomycin, doxorubicin, daunomycin, mitomycin C, actinomycin), antiestrogen drug (e.g., tamoxifen, fulvestrant, toremifene, raloxifene, droloxifene), anti-androgen drug (e.g., bicalutamide, flutamide, nilutamide), LHRH antagonist or LHRH agonist (e.g., goserelin, leuprolide, and buserelin), aromatase inhibitor (e.g., anastrozole, letrozole), CYP17 cleavage enzyme inhibitor (such as abiraterone), anti erbB2 antibody trastuzumab [Herceptin], anti-EGFR antibody cetuximab [Erbitux]; inhibitor of tyrosine kinase, serine/threonine kinases (e.g., imatinib, nilotinib, sorafenib, trametinib, crizotinib); cyclin-dependent kinase inhibitor (e.g., CDK4 inhibitor, palbociclib), anti-human vascular endothelial growth factor antibody of bevacizumab (Avastin) and VEGF receptor tyrosine kinase inhibitor (apatinib); antitumor immunotherapy, such as anti-PD-1 antibody (pembrolizumab, nivolumab), anti-PD-Li antibody, anti-LAG-3 antibody, anti-CTLA-4 antibody, anti-4-1BB antibody, anti-GJTR antibody, anti-ICOS antibody, interleukin 2.

Definitions

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

For the purpose of identifying a certain impurity of Compound 4 (or a pharmaceutically acceptable salt thereof), a relative retention time (RRT) may be used to describe the impurity. The relative retention time for a particular impurity in a particular HPLC method (e.g., Example 1) is determined by dividing the retention time measured for the impurity ($RT_{Impurity}$) (e.g., measured in minutes) by the retention time measured for Compound 4 ($RT_{Compound\ 4}$) (e.g., measured in minutes), i.e. according to the following formula: $RRT=RT_{Impurity}/RT_{Compound\ 4}$. Hence, impurities having a RRT<1 (e.g., 0.88) elute (e.g., from the HPLC column) before Compound 4, and impurities characterized by a RRT of >1 (e.g., 1.04) elute after Compound 4. Those skilled in the art would understand that using the HPLC method described in Example 1, the retention time for Compound 4 or its pharmaceutically acceptable salt would be the same, not considering the retention time of the counterion(s). Similarly, impurities such as impurity A or B as defined herein, whether exist as a basic or a protonated form, would have the same retention time when using the HPLC method described in Example 1. For the purpose of this disclosure, impurity A or B includes any form that may exist in a test sample.

The terms "purity" and "impurities" are used according to their respective art accepted meaning. The term "purity by HPLC area", "purity by HPLC", or purity "as measured by HPLC," refers to the purity of the respective compound as measured using an HPLC method, e.g., the HPLC method described in Example 1, expressed as HPLC area percentage. For the purpose of this disclosure, a purity of a compound herein measured by the HPLC method described in Example 1 can be expressed as an area percentage of the peak representing the compound using either 220 nm or 254 nm as a detection wavelength. For example, in some embodiments, unless otherwise specified or contrary from context, when a compound herein is said to have a purity by HPLC of about 95%, it can mean that when measured by the HPLC method described in Example 1, the peak representing the compound has an area percentage of about 95% using either one or both of 220 nm and 254 nm as the detection wavelength. In any of the embodiments described herein, unless otherwise specified or contrary from context, the purity of a compound herein by HPLC can be measured by the HPLC method described in Example 1, and expressed as the area percentage of the peak representing the compound in an HPLC trace using 220 nm as the detection method. The relevant amount of impurities should be understood similarly. See examples of representative purity by HPLC in FIGS. 4A, 4B, 5A, and 5B. For example, in FIG. 4A, the Compound 4 has a purity by HPLC of 97.5% (peak area with retention time 10.976, which represents Compound 4), and the impurity A is present at a level of 1.26% (peak area with retention time 11.638, which represents impurity A) and impurity B is present at a level of 0.23% (peak area with retention time 9.680, which represents impurity B). Although weight percentage purity of a test sample can also be established by HPLC methods, as used herein, unless specifically referenced as purity by weight, the purity terms such as purity by HPLC or measured by HPLC, or analogous terms should not be understood as referring to purity by weight.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

The term "leaving group" is given its ordinary meaning in the art of synthetic organic chemistry, which for example can refer to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some embodiments, hydroxyl group or an alkoxy group can also be a leaving group herein.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "therapeutically effective amount," as used herein, refers to that amount of a therapeutic agent (e.g., Compound 4 or 5) sufficient to result in amelioration of one or more symptoms of a disorder or condition (e.g., lung cancer), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

EXAMPLES

Example 1. General Methods

Materials: the starting materials, reagents, solvents, etc. are generally available through commercial sources.

POWDER X-RAY DIFFRACTION (XRPD): The solid samples from screening were examined using X-ray diffractometer (Bruker D8 advance). The system is equipped with LynxEye detector. The samples were scanned from 3 to 40° 2θ, at a step size 0.02° 2θ. The tube voltage and current were 40 KV and 40 mA, respectively. The sample was transferred from sample container onto zero background XRD-holder and gently ground.

TGA ANALYSIS: TGA analysis was carried out on a TA Instruments TGA Q500. Samples was placed in a tarred platinum or aluminum pan, automatically weighed, and inserted into the TGA furnace. The samples were heated at a rate of 10° C./min to final temperature. The purge gas is nitrogen for balance at 40 ml/min and for the sample at 60 ml/min, respectively.

DSC ANALYSIS: DSC analysis was conducted on a TA Instruments Q200. The calibration standard was indium. A sample in weight was placed into a TA DSC pan, and weight accurately recorded. Crimped pans were used for analysis and the samples were heated under nitrogen (50 mi/min) at a rate of 10° C./min, up to a final temperature.

Particle Size Analysis:

The particle size distribution is tested by Laser Particle Size Analyzer.

| Test Method for Particle Size Distribution | | |
|---|---|---|
| Instrument and Equipment | Malvern Mastersizer 3000 Particle Size Analyzer or other equivalent Sample dispersion units: Hydro 3000MU or other equivalent Software: Malvern software Mastersizer 3000 or other equivalent | |
| Method Parameters | Pump Speed: 2500 rpm/min Models: General Purpose Lower/Upper Limit of Obscuration: 10%/20% Particle: Irregular Sample Measurement Time: 12 s Refractive index: 1.59 Create Average Result: Select | Dispersant Volume: 800 mL Sensitivity: Normal Dispersant Name: Water or IPA Background Measurement Time: 12 s Measurement Cycles: 3 Delay: 1 sec |
| Sample Preparation | Appropriate weigh a certain amount of sample (for example 200 mg) into a glass vial, and add 1 mL of 1% Tween 80 in order to soak sample, and then add some water to disperse thoroughly on Circular oscillator (sonication could be used if necessary) | |

HPLC ANALYSIS: a representative HPLC method is shown below, which can be used, for example, to analyze the purity of the compounds herein.

Instrument: Agilent
Flow rate: 1.0 mL/min
Mobile phase: A: 0.01% TFA in water
  B: $CH_3CN$
Injection volume: 5 μL
Column: Agilent Zorbax Bonus RP, 3.5 um, 4.6*150 mm
Column Temperature: 25° C.
Detection: 220 or 254 nm
Run Time: 30 minutes Gradient (T/B %): 0.0/10, 15.0/40, 20.0/90, 30.0/90, 31.0/10 and 35.0/10

Example 2. Preparation of N-(2-((2-(dimethyl-amino)ethyl)(methyl)amino)-4-methoxy-5-((4-(1-(2,2,2-trifluoroethyl)-1H-indol-3-yl)pyrimidin-2-yl)amino)phenyl)acrylamide monomesylate

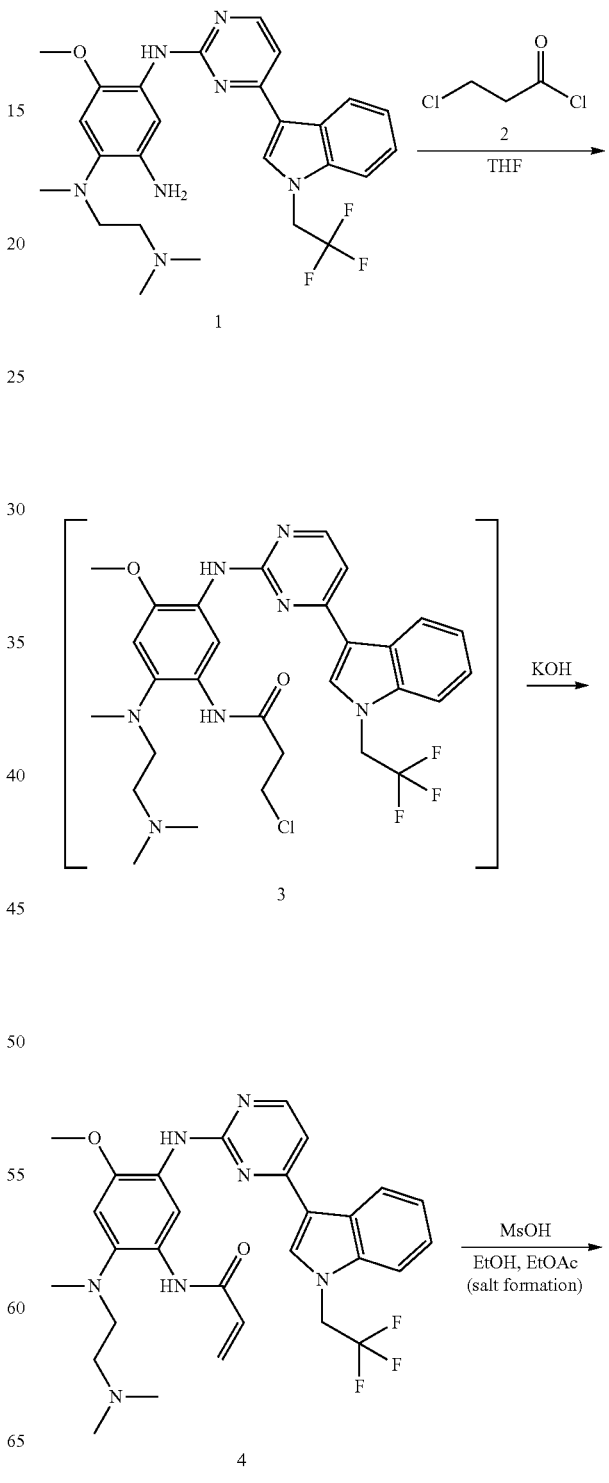

-continued

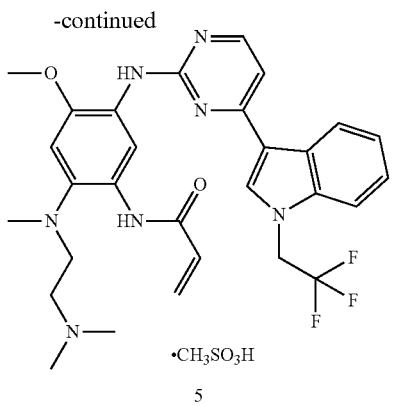

5

Compound 1 can be prepared following the same procedure as described in US Publication No. 2017/0355696 A1, published on Dec. 14, 2017, the content of which is hereby incorporated by reference in its entirety. In US Publication No. 2017/0355696 A1, compound 1 was prepared by reducing the corresponding nitro precursor using Fe/NH$_4$Cl. It was found that this transformation can also be carried out using Pd/C under H$_2$.

Compound 1 (1 eq) was mixed with tetrahydrofuran (about 10 mL/g of compound 1) and water (about 1 ml/g of compound 1) under N$_2$. The mixture was cooled to −10 to −5° C. Compound 2 (1.2 eq) was then added to the mixture, with temperature controlled to −10 to 0° C. during the addition. After which, the mixture was stirred at that temperature for about 30 minutes. Then, KOH (3.8 eq) was added to the mixture portion-wise, and the temperature was controlled to below 20° C. during KOH addition. After which, the reaction mixture was heated to 55-65° C. and held at that temperature for about 16 hours before it was cooled to 25° C. or below. After workup and purification, compound 4 was obtained with greater than 98.5% purity by HPLC. Optionally, compound 4 can be dissolved in isopropanol/water (5:1, total volume of about 8 ml/g of compound 4) at 75-85° C., and then cooled slowly to 40-50° C., held for 1-2 hours with stirring, and then slowly cooled to 10-20° C. and stir for 2 hours. The solid precipitated out was then collected, washed and dried to provide compound 4 with greater than 98.5% purity by HPLC.

Analytical data for Compound 3: LCMS (ESI, m/z): [M+H]$^+$=604.0; HNMR (400 MHz, DMSO-d$_6$, ppm): δ 10.39 (brs, 1H), 9.83 (s, 1H), 8.63 (s, 1H), 8.58 (s, 1H), 8.37 (d, J=5.6 Hz, 1H), 8.35 (m, 1H), 8.06 (s, 1H), 7.72 (d, J=8.0 Hz, 1H), 7.29 (m, 1H), 7.26 (d, J=5.6 Hz, 1H), 7.26 (m, 1H), 6.95 (s, 1H), 5.34 (q, J=9.2 Hz, 2H), 3.90 (t, J=6.4 Hz, 2H), 3.88 (s, 3H), 3.31 (m, 2H), 3.28 (m, 2H), 3.11 (t, J=6.4 Hz, 2H), 2.75 (s, 6H), 2.63 (s, 3H). CNMR (100 MHz, DMSO-d$_6$, ppm): 168.90, 161.68, 160.59, 158.38, 147.62, 139.42, 138.02, 133.39, 125.79, 125.04, 124.88, 123.30, 122.33, 122.03, 117.80, 115.07, 111.28, 107.85, 104.68, 56.51, 53.95, 49.30, 46.98, 43.47, 42.65, 41.59, 39.46. FNMR (376 MHz, DMSO-d$_6$, ppm): δ −69.92 (3F).

Compound 4 (1 eq) was then dissolved in ethanol and ethyl acetate (1:1, combined volume of about 10 mL/g compound 4). The mixture was heated to 55-65° C. and methanesulfonic acid (0.95 eq) was added under N$_2$. The reaction was kept at this temperature for about 20-30 minutes. The reaction mixture was then cooled down slowly to obtain the mesylate salt compound 5 in Form I, which is used as seed crystals. A representative $^1$H NMR of compound 5 is shown in FIG. 1.

The above cooling can be performed in the presence of seed crystals, for example, after adding seed crystals into the reaction mixture (e.g., about 3% to about 15% w/w). The mixture with the seed crystals can be first slowly cooled to 45-55° C., held for about 2 hours with stirring, then slowly cooled to 35-45° C., held for 1-2 hours with stirring, and then slowly cooled to 25-35° C., held for 1-2 hours with stirring, then slowly cooled to 15-25° C. and stir for at least 2 hours. The solid resulted was then filtered and collected to provide pure compound 5. In one example, 3% by weight of seed crystals were added into the reaction mixture before the step-wise cooling step. The crystals obtained were analyzed for particle size distribution as described herein. This batch of crystals were found to have a D90: about 82.4 um; D50: about 34.3 um; and D10 of about 11.4 um.

Compound 5 can also be prepared by adding 25 to 50 mole % of methanesulfonic acid to a solution of Compound 4 in ethyl acetate and ethanol at 50-60° C. and seed crystals (e.g., about 3% to about 15% w/w) under N$_2$. The reaction was kept at this temperature for about 30 minutes and the remaining 50 to 75 mole % of methanesulfonic acid was added. The mixture with the seed crystals can be first slowly cooled to 45-55° C., held for about 2-3 hours with stirring, then slowly cooled to 40-50° C., held for 1-2 hours with stirring, and then slowly cooled to 30-40° C., held for 1-2 hours with stirring, then slowly cooled to 20-30° C. and stir for about 2-3 hours. The solid resulted was then filtered and collected to provide pure compound 5. This solid can be further treated in isopropanol and water by stirring at 55-65° C. for 10-12 hours and then slowly cooled to 40-50° C., held for 1-2 hours with stirring, and then slowly cooled to 30-40° C., held for 1-2 hours with stirring, then slowly cooled to 20-30° C. and stir for 1-2 hours.

Typically, compound 5 obtained by this procedure has a purity of greater than 98.5% by HPLC.

Example 2A. Alternative Preparation of N-(2-((2-(dimethylamino)ethyl)(methyl)amino)-4-methoxy-5-((4-(1-(2,2,2-trifluoroethyl)-1H-indol-3-yl)pyrimidin-2-yl)amino)phenyl)acrylamide monomesylate

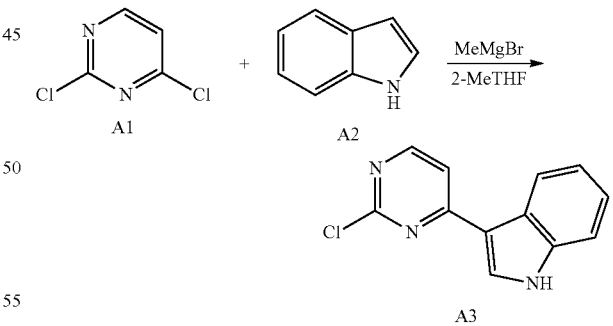

Compound A1 (1 eq) was mixed with 2-methyl tetrahydrofuran (about 10 mL/g of compound A1) under N$_2$. The mixture was cooled to −5 to 5° C. MeMgBr (0.85 eq) was added to the mixture, with temperature controlled between −5 to 5° C. After which, compound A2 (1.1 eq) was added in one portion between −5 to 5° C. After stirring for 1 hour, the mixture was heated to 78 to 83° C. and stirred for another 1 hour. MeMgBr (0.44 eq) was added to the mixture, with temperature controlled between 78 to 83° C., and the mixture was stirred for another 0.5-1 hour. Followed the similar procedure above, two portions of MeMgBr (0.44 eq for each portion) were added to the mixture. The mixture was heated at 78 to 83° C. for 19-21 hours under N₂, and then cooled to 0-5° C. Aqueous HOAc (12%, 3.3 eq) was added to quench the reaction, with temperature controlled below 40° C. The mixture was separated, and the aqueous phase was extracted with EtOAc (2 g/g of compound A1). The combined organic layer was washed with brine (5 g/g of compound A1), and then was concentrated at 45-50° C. to a volume of 2-3 mL/g of compound 1. EtOH (4 g/g of compound A1) was added to the residue, and the mixture was concentrated to a volume of 3-4 mL/g of compound A1. The residue was heated to 70-75° C. for 1 hour and cooled to 20-25° C. Water (3 g/g of compound A1) was added, and the mixture was stirred for 2 hours. Filtered and the filter cake was dried at 60-65° C. under vacuum to afford compound A3.

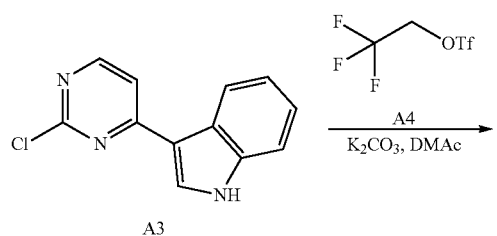

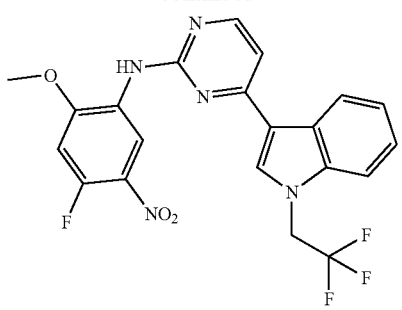

Compound A5 was mixed with compound A6 (1.1 eq), p-TSA (0.2 eq) and isopropanol (9 g/g of compound A5) under N₂. The mixture was heated at 77-87° C. for 16-20 hours, and then cooled to 30-40° C. Filtered and the filter cake was washed with isopropanol and water respectively, dried under vacuum at 60-65° C. to afford compound A7 HCl salt. The HCl salt was dissolved in DMF (11 mL/g of HCl salt) and Et₃N (1.2 eq) was added, followed by addition of water (11 mL/g of HCl salt). The mixture was stirred at 25-30° C. for 1-2 hours and filtered. The filter cake was washed with water and dried under vacuum at 60-65° C. to afford compound A7.

Compound A3 was mixed with DMAc (10 mL/g of compound A3) under N₂. K₂CO₃ (1.5 eq) was added and the mixture was stirred at 15-20° C. for 1.5-2 hours. Compound A4 (1.15 eq) was added, and the mixture was heated at 40-45° C. for 16-20 hours. Water (10 g/g of compound A3) was added, with temperature controlled below 20° C. The mixture was cooled to 0-5° C. and stirred for 1.5-2 hours. The mixture was filtered, and the filter cake was washed with water and EtOAc respectively, and dried under vacuum at 60-65° C. to afford compound A5.

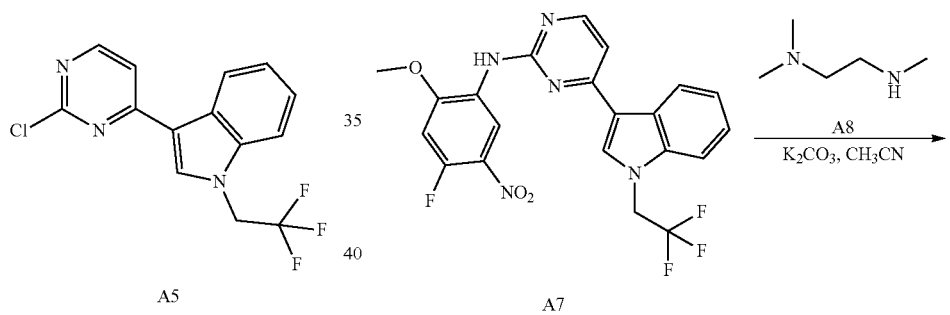

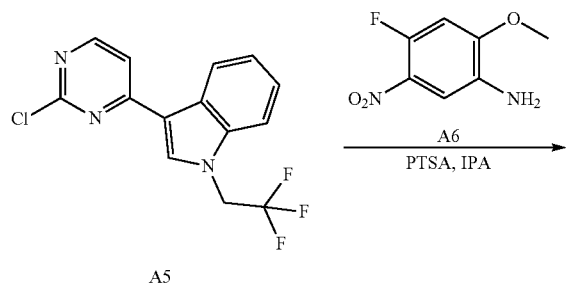

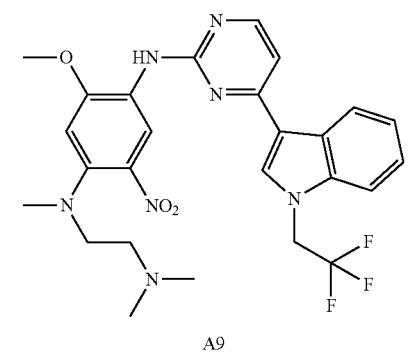

Compound A7 was mixed with K₂CO₃ (1.3 eq) and MeCN (10 mL/g of compound A7) under N₂. Compound A8 (1.4 eq) was added to the mixture, with temperature controlled at 15-30° C. The mixture was heated at 77-87° C. for 2-4 hours, followed by addition of water (15 mL/g of compound A7). The mixture was stirred at 10-20° C. for 2-4 hours and filtered. The filter cake was washed with water and dried under vacuum at 45-50° C. to afford compound A9.

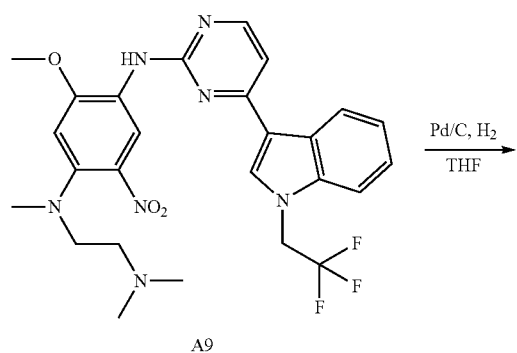

A9

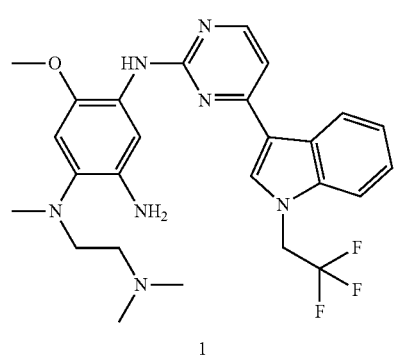

1

Compound A9 was mixed with Pd/C (0.1 g/g of compound A9) and THF (10 mL/g of compound A9) under $N_2$. The mixture was changed from $N_2$ to $H_2$ atmosphere, and heated at 30-40° C. The mixture was stirred at $H_2$ atmosphere (0.1-0.2 MPa) for 9-11 hours, and then changed to $N_2$ atmosphere, cooled to 15-25° C. and filtered through Celite. For the filtrate, a solvent switch from THF to EtOAc was performed by distillation with additional amounts of EtOAc (3×10 mL/g of compound 9). The mixture was heated at 50-60° C. to reach a clear solution and then cooled down slowly to 0-10° C. to precipitate out solid. The suspension was stirred at 0-10° C. for 4-5 hours and then filtered. The filter cake was washed with EtOAc and dried under vacuum at 40-45° C. to afford compound 1.

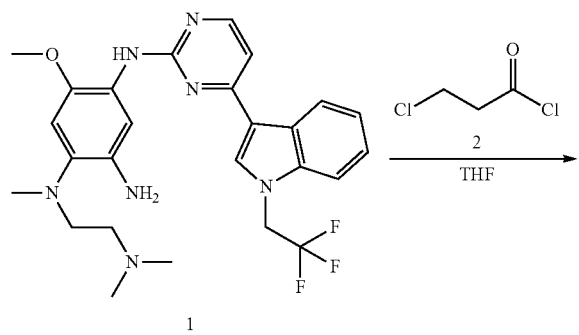

1

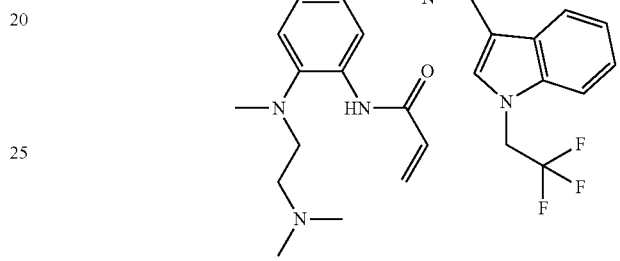

3

4

Figure 4A:
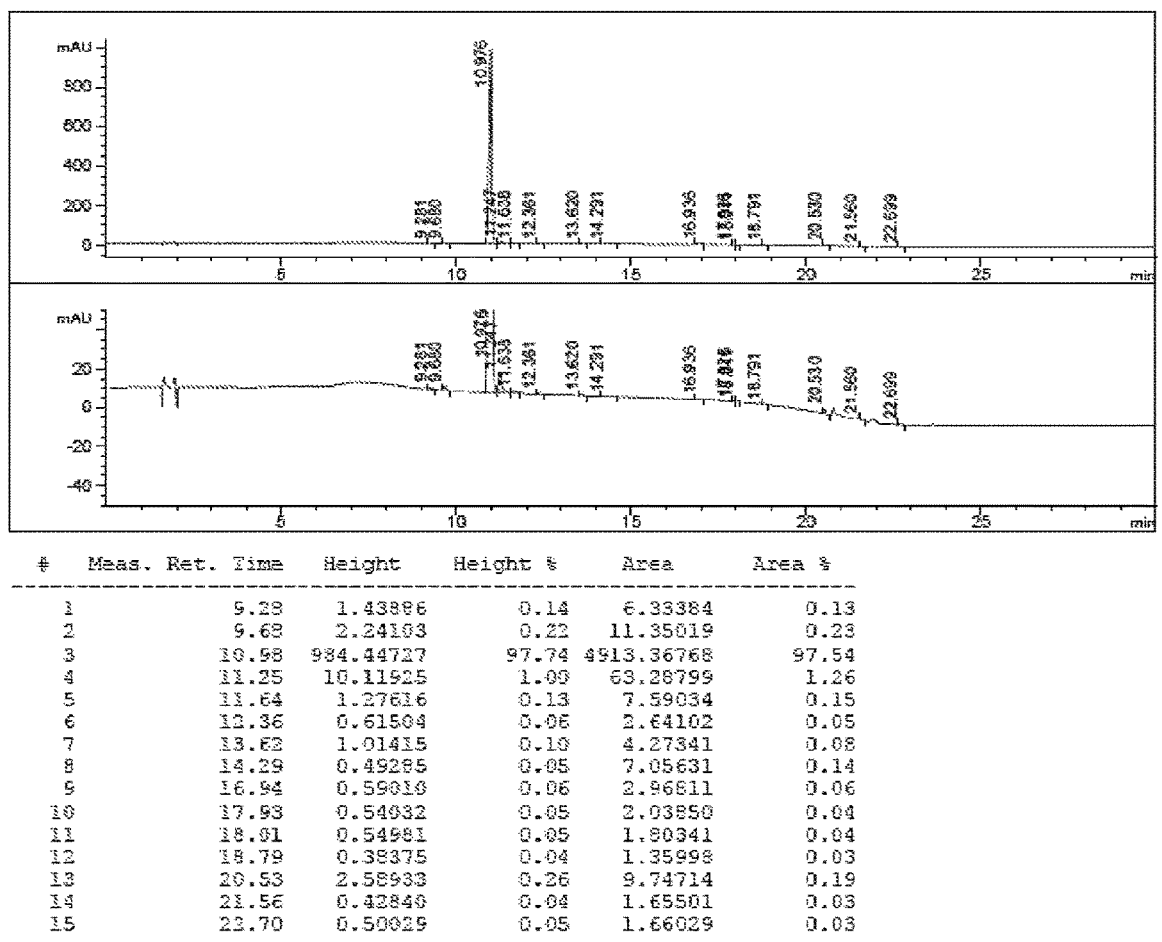
FIG. 4A shows a representative HPLC trace of Compound 4 produced by the methods herein, without the step of recrystallization in isopropanol (IPA) and water.
Figure 4B:
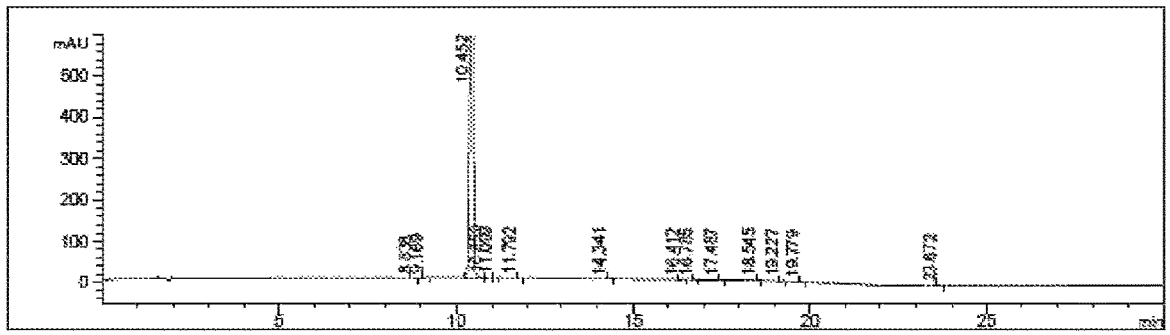
FIG. 4B shows a representative HPLC trace of Compound 4 after recrystallization from IPA and water.
Figure 4B:
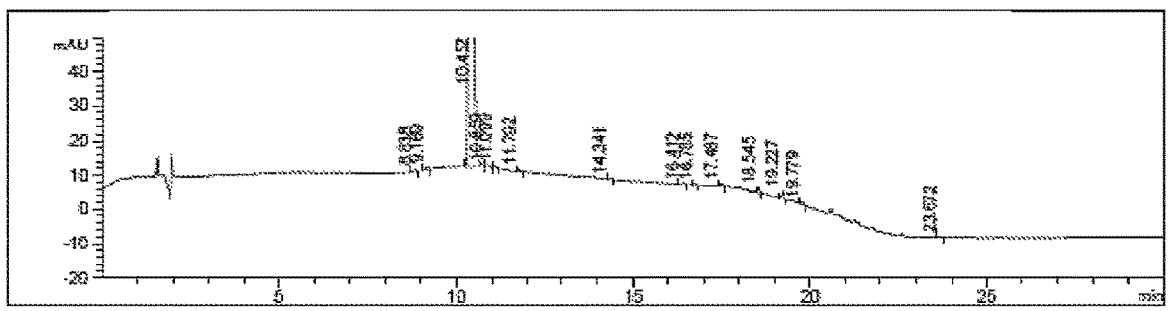

Compound 1 (1 eq) was mixed with tetrahydrofuran (about 10 mL/g of compound 1) and water (about 1 mL/g of compound 1) under $N_2$. The mixture was cooled to −10 to −5° C., and compound 2 (1.2 eq) was added with temperature controlled to −10 to 0° C. during addition. After which, the mixture was stirred at −10 to 0° C. for about 30 minutes. The reaction was taken a sample to run HPLC to make sure compound 1 was converted completely (compound 1≤0.5%). Then, KOH (4.8 eq) was added to the mixture, and the temperature was controlled below 20° C. during addition. After which, the reaction mixture was heated to 55-65° C. and maintained at that temperature for about 16 hours. A sample was taken from the reaction to run HPLC to ensure the reaction endpoint (compound 3≤0.2%) before it was cooled to 15-25° C. Water (9 g/g of compound 1) was added and the mixture was separated. The organic layer was diluted with EtOAc (10 mL/g of compound 1) and washed with brine and water twice, respectively. A switch of solvent from EtOAc to isopropanol was performed by distillation with additional amounts of isopropanol (2×12 g/g of compound 1). Water (1.4 g/g of compound 1) was added, and the mixture was heated at 75-85° C. to reach a clear solution, then cooled to 10-20° C. slowly to precipitate out solid. The suspension was stirred at 10-20° C. for 2-3 hours and filtered. The filter cake was washed with isopropanol/water (5:1) and dried under vacuum at 45-50° C. to afford compound 4. It was found that by using an additional crystallization procedure, the purity of compound 4 can be further enhanced, with impurity A (relative retention time, about 1.02) and impurity B (relative retention time, about 0.88) reduced to below 0.2% as tested by the HPLC method in Example 1, area % calculated based on 220 nm detection. See FIG. 4A (prior to crystallization in IPA/Water) and FIG. 4B (after crystallization from IPA/Water). Retention time of compound 4 in FIG. 4A is 10.976 min and in FIG. 4B is 10.452 min. The combined yield from aniline 1 to compound 4 is about 70%.

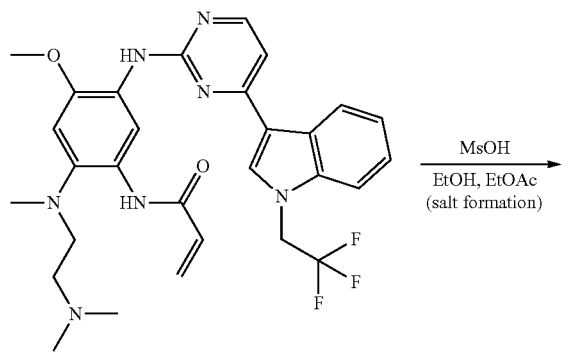

4

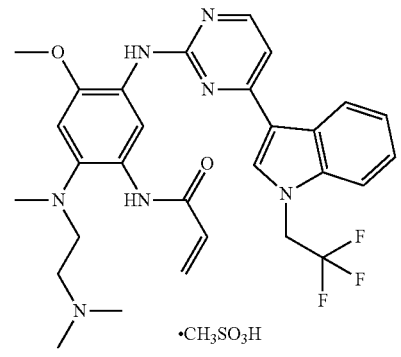

·CH₃SO₃H

5

Figure 5A:
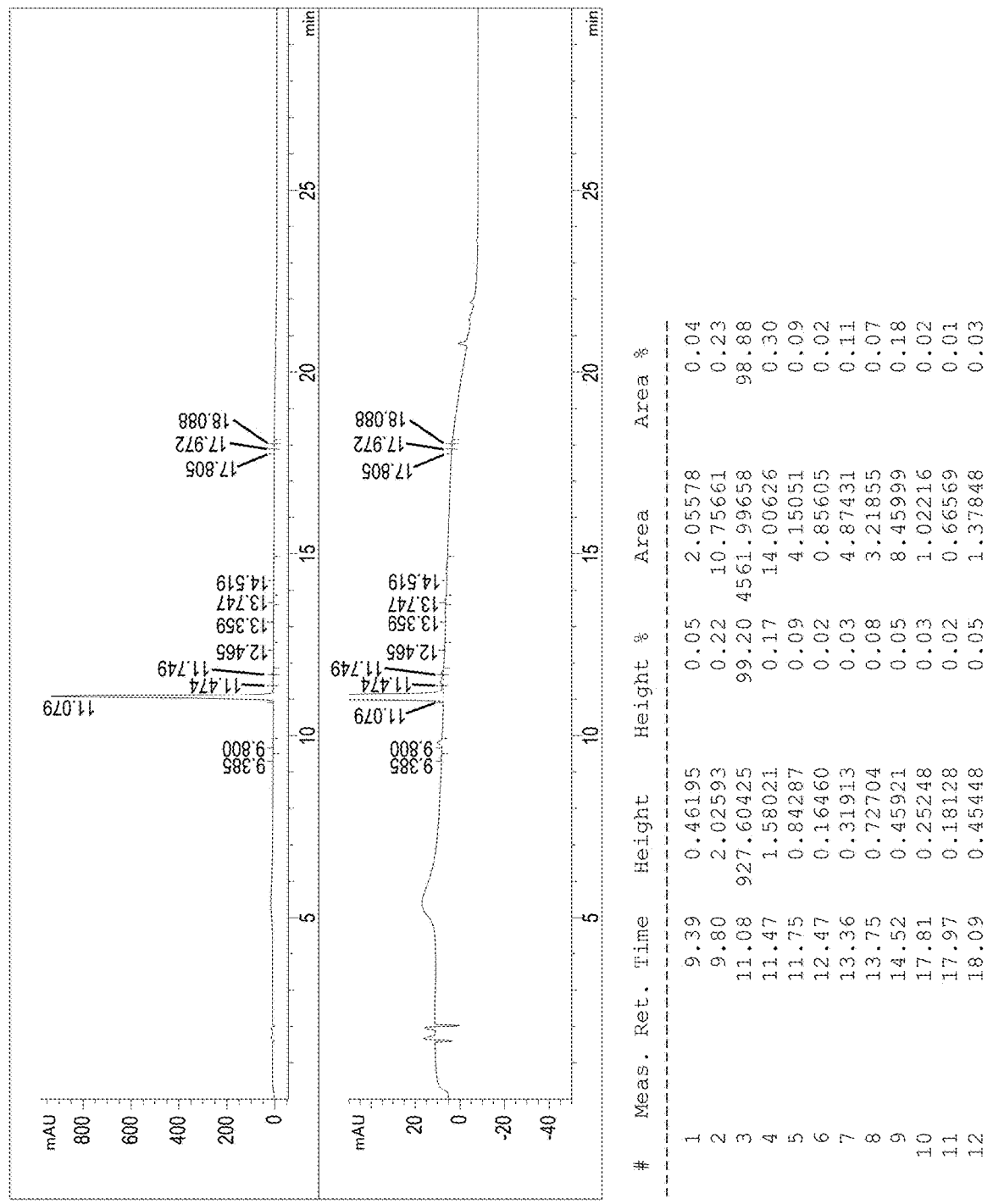
FIG. 5A shows a representative HPLC trace of Compound 5 obtained from salt formation of Compound 4 that was not further purified with recrystallization in IPA and water.
Figure 5B:
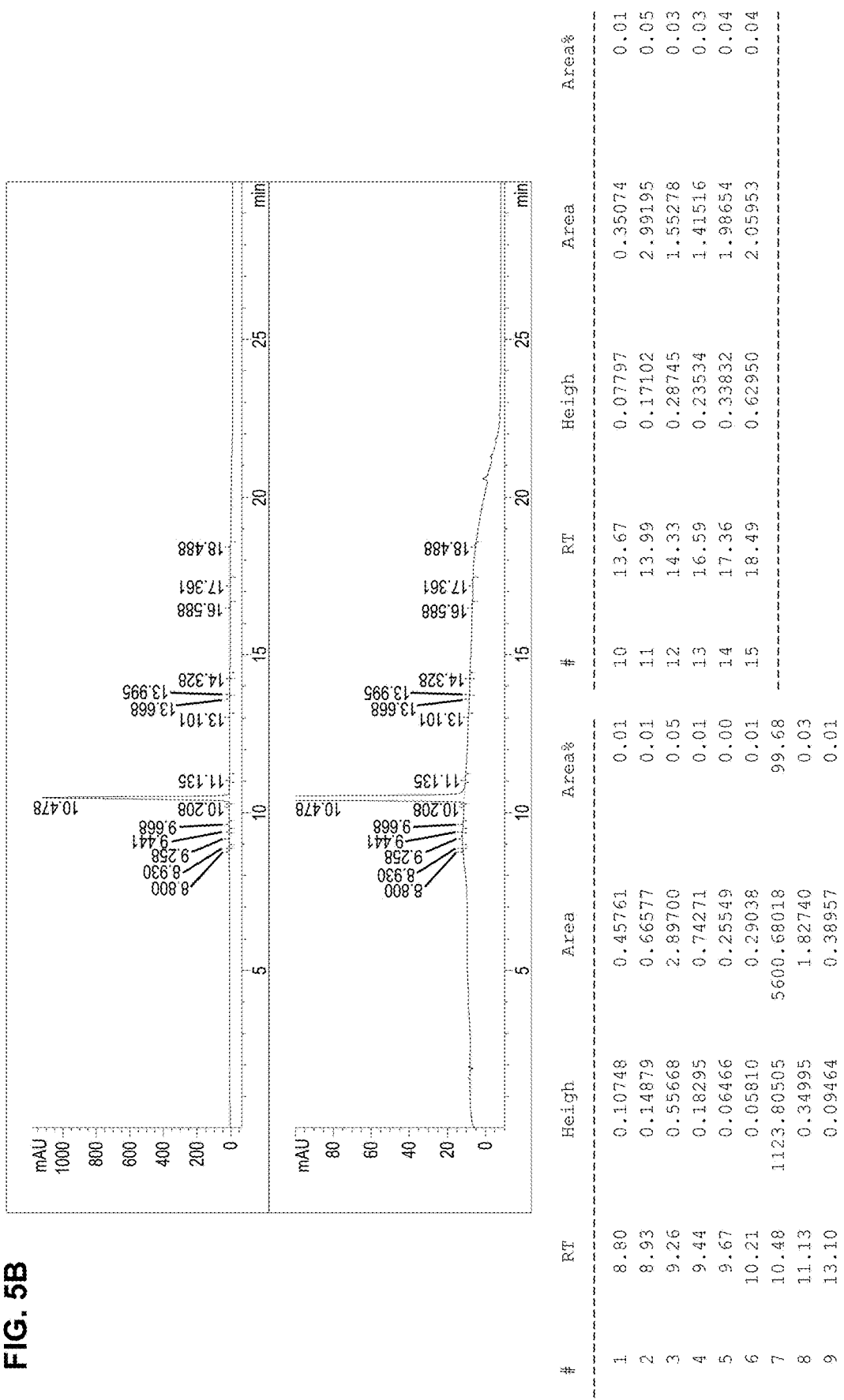
FIG. 5B shows a representative HPLC trace of Compound 5 obtained from salt formation of Compound 4 that was further purified with recrystallization in IPA and water.

Compound 4 (1 eq) was dissolved in ethanol and ethyl acetate (1:1, combined volume of about 12 mL/g compound 4). The mixture was heated to 55-60° C. and methanesulfonic acid (0.24 eq) was added under $N_2$. After adding seed crystals into the reaction mixture (e.g., about 3% to about 15% w/w), additional methanesulfonic acid (0.71 eq) was added at 55-60° C. The mixture was stirred at 55-60° C. for 2-3 hours, and then slowly cooled to 45-55° C. and held for about 2 hours with stirring. Then the mixture was slowly cooled to 35-45° C., and held for 1-2 hours with stirring. Then the mixture was slowly cooled to 25-35° C., held for 1-2 hours with stirring. Then the mixture was slowly cooled to 15-25° C. and stirred for at least 2 hours. The mixture was then filtered and the solid was collected to afford wet compound 5. Wet compound 5 was slurried in mixed solvents of isopropanol and water (7:0.4, 7.4 mL/g of compound 4), and the suspension was applied wet milling to control particle size (D50: 30-60 um, D90: 80-120 um). After milling, the suspension was filtered and the filter cake was dried under vacuum at 40-50° C. to afford compound 5. Compound 5 obtained has an HPLC purity of greater than 99% (HPLC method of Example 1, area % based on 220 nm detection). It is noted that when impurity B was not removed during the process of preparing compound 4, the formation of mesylate salt did not remove this impurity as evidenced by FIGS. 5A and 5B. FIG. 5B is the HPLC trace obtained with salt formation of compound 4 that was further purified with recrystallization in IPA/Water as described above; FIG. 5A is the HPLC trace obtained with salt formation of compound 4 that was not further purified with recrystallization in IPA/Water as described above. As understood by those skilled in the art, for the HPLC purity determination, it is not critical whether impurity A or B is present in a salt form after the salt formation step, as under the HPLC condition with the method of Example 1, the protonation state of impurity A or B in the sample is not important for its retention time observed in HPLC. Retention time of compound 5 in FIG. 5A is 11.079 m and in FIG. 5B is 10.478 m. Example 3. Solid State Analysis of Compound 5 Form I The crystals obtained from Example 2 were analyzed by XRPD and DSC, and was named as Form I. A representative XRPD spectrum was shown in FIG. 2A. (See also Table 1 below for a list of peaks with relative intensities). A representative DSC spectrum was shown in FIG. 2B.

TABLE 1

| XRPD Peaks | |
|---|---|
| Angle 2-Theta/° | Intensity % |
| 6.134 | 10.2 |
| 6.565 | 9.9 |
| 7.802 | 100 |
| 8.476 | 9.9 |
| 10.189 | 26.9 |
| 10.773 | 37.2 |
| 11.239 | 18.9 |
| 11.871 | 8.5 |
| 12.119 | 10 |
| 13.213 | 8.7 |
| 13.605 | 23.5 |
| 13.883 | 28.8 |
| 14.628 | 6.4 |
| 14.977 | 12.5 |
| 15.712 | 9 |
| 16.053 | 9.2 |
| 16.409 | 34.7 |
| 17.729 | 65 |
| 18.376 | 27.2 |
| 18.651 | 18.7 |
| 18.903 | 32.2 |
| 18.903 | 32.2 |
| 19.212 | 31.1 |
| 19.476 | 11.5 |
| 19.776 | 41.9 |
| 20.572 | 25.3 |
| 20.85 | 17.3 |
| 21.13 | 14.9 |
| 21.356 | 9.9 |
| 22.17 | 6.4 |
| 22.591 | 15.3 |
| 22.873 | 7.3 |
| 23.267 | 5.9 |
| 23.463 | 11.5 |
| 23.684 | 36.2 |
| 23.924 | 54 |
| 24.453 | 7.5 |
| 24.919 | 19.4 |
| 25.314 | 7.2 |
| 25.902 | 11.5 |
| 26.541 | 11.4 |
| 26.97 | 4.3 |
| 27.337 | 7 |
| 27.756 | 17.7 |
| 28.17 | 3.4 |
| 28.583 | 7.9 |
| 29.294 | 3.6 |
| 30.313 | 3.3 |
| 30.62 | 2.5 |
| 31.046 | 5 |
| 31.613 | 3.6 |
| 31.967 | 4.3 |
| 33.189 | 5.3 |
| 33.521 | 4.1 |
| 34.088 | 3.9 |
| 35.375 | 4.1 |
| 36.025 | 3.1 |

TABLE 1-continued

XRPD Peaks

| Angle 2-Theta/° | Intensity % |
|---|---|
| 37.588 | 2.5 |
| 38.066 | 2.1 |
| 38.748 | 3.1 |
| 39.249 | 2.5 |

Figure 3:
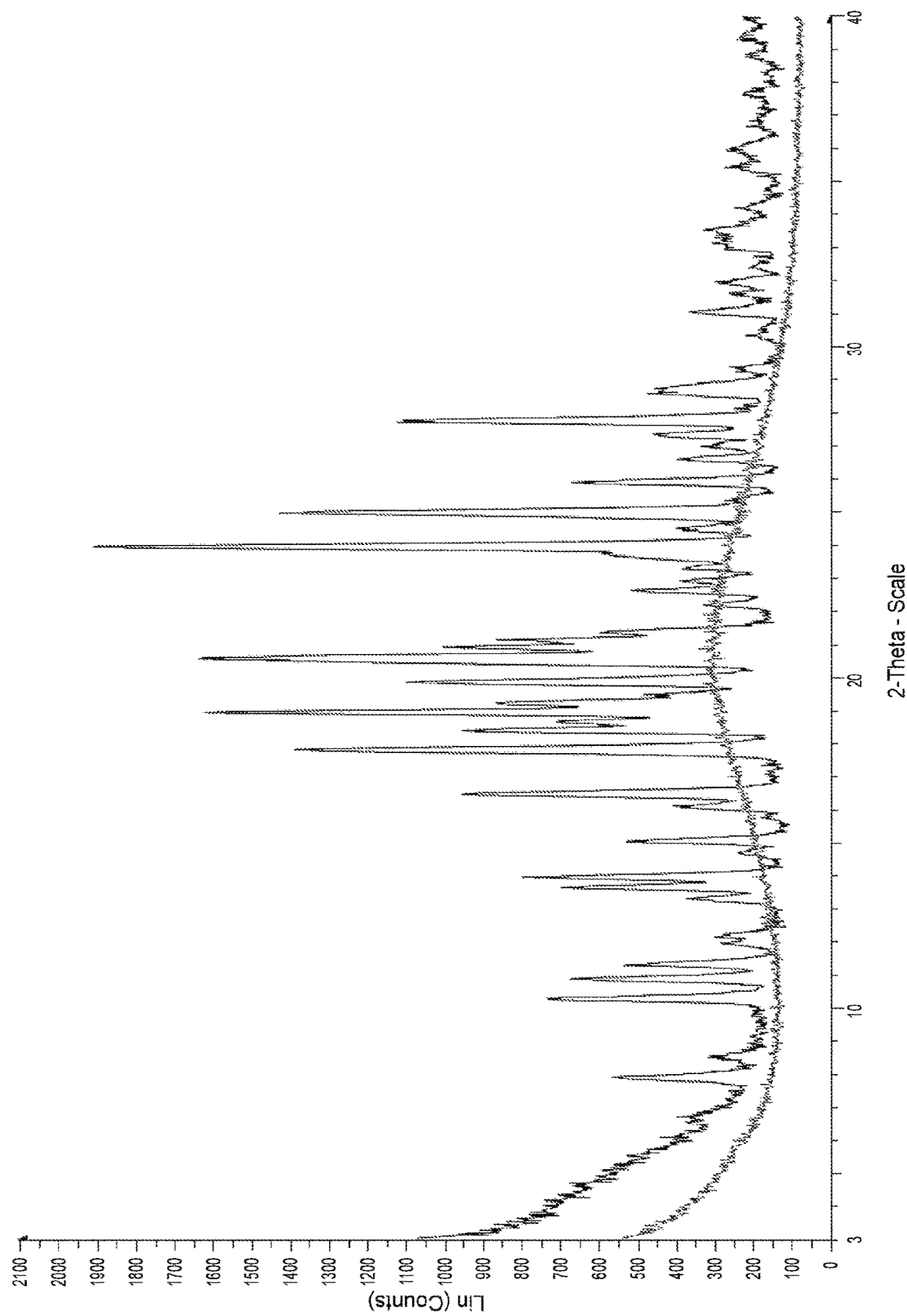
FIG. 3 shows XRPD spectra from a thermo treatment experiment with Form I. The XRPD overlay of the sample (after the treatment) and the initial drug indicates conversion of Form I into an amorphous form after the thermo treatment.

It was also found that Form I can be converted into an amorphous form upon thermal treatment by heating the crystals in DSC cells to 220° C. and then immediately placed into ice ("quench"). See e.g., FIG. 3. Also, when Form I was grinded mechanically, some loss of crystallinity of Form I was observed, though no new crystalline form was identified.

TGA profile showed that there was 0.1935% weight loss prior to decomposition. DSC profile showed that there was an endothermic peak due to melting with onset and peak temperatures of 208.64° C. and 210.12° C., respectively, enthalpy of 96.87 J/g.

It was also found that crystalline Form I is non-hygroscopic. Upon storing at 25° C. at a relative humidity of 80%, only negligible increase in weight was observed.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. Crystals of crystalline form I of N-(2-((2-(dimethylamino)ethyl)(methyl)amino)-4-methoxy-5-((4-(1-(2,2,2-trifluoroethyl)-1H-indol-3-yl)pyrimidin-2-yl)amino)phenyl)acrylamide monomesylate, wherein the crystalline form I is characterized by an XRPD pattern having four or more of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°, and the crystals are characterized by a particle size distribution of:

1) D90: about 150 µm to about 250 um; D50: about 90 µm to about 140 µm; and D10 of about 40 µm to about 75 um;
2) D90: about 100 µm to about 150 um; D50: about 20 µm to about 60 µm; and D10 of about 5 µm to about 15 um;
3) D90: about 120 µm to about 200 um; D50: about 50 µm to about 100 µm; and D10 of about 10 µm to about 20 um;
4) D90: about 140 µm to about 180 um; D50: about 90 µm to about 130 µm; and D10 of about 55 µm to about 85 um;
5) D90: about 50 µm to about 100 um; D50: about 20 µm to about 30 µm; and D10 of about 3.5 um to about 9 um;
6) D90: about 70 µm to about 95 um; D50: about 25 µm to about 40 µm; and D10 of about 5 µm to about 15 um;
7) D90: about 120 µm to about 160 um; D50: about 55 µm to about 85 µm; and D10 of about 5 µm to about 15 µm; or
8) D90: about 90 µm to about 130 um; D50: about 35 µm to about 60 µm; and D10 of about 10 µm to about 15 um.

2. The crystals of claim 1, wherein the crystalline form I is characterized by an XRPD spectrum having eight or more of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°.

3. The crystals of claim 1, wherein the crystalline form I is characterized by an XRPD spectrum having sixteen or more of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°.

4. The crystals of claim 1, wherein the crystalline form I is characterized by an XRPD spectrum having all of the following peaks: 7.8, 10.2, 10.8, 11.2, 13.6, 13.9, 15.0, 16.4, 17.7, 18.4, 18.7, 18.9, 19.2, 19.8, 20.6, 20.8, 21.1, 22.6, 23.7, 23.9, 24.9, 25.9, and 27.8 degrees 2 theta, ±0.2°.

5. A pharmaceutical composition comprising the crystals of claim 1, and optionally a pharmaceutically acceptable excipient or carrier.

6. The pharmaceutical composition of claim 5, which is in the form of a tablet or capsule.

7. A method of treating lung cancer, the method comprising administering to a subject in need thereof a therapeutically effective amount of the crystals of claim 1.

8. The method of claim 7, wherein the lung cancer is mediated by an EGFR variant, which is an L858R mutant, Exon19 deletion mutant, and/or T790M mutant.

9. The method of claim 7, wherein the lung cancer is non-small cell lung cancer.

10. The method of claim 7, wherein the subject is resistant to one or more EGFR inhibitors chosen from gefitinib, erlotinib, and icotinib.

11. The method of claim 7, wherein the crystals are administered to the subject orally.

12. The method of claim 8, wherein the cancer is non-small cell lung cancer.

13. The crystals of claim 1, characterized by a particle size distribution of: D90: about 150 µm to about 250 um; D50: about 90 µm to about 140 µm; and D10 of about 40 µm to about 75 um.

14. The crystals of claim 1, characterized by a particle size distribution of: D90: about 100 μm to about 150 um; D50: about 20 μm to about 60 μm; and D10 of about 5 μm to about 15 um.

15. The crystals of claim 1, characterized by a particle size distribution of: D90: about 120 μm to about 200 um; D50: about 50 μm to about 100 μm; and D10 of about 10 μm to about 20 um.

16. The crystals of claim 1, characterized by a particle size distribution of: D90: about 140 μm to about 180 um; D50: about 90 μm to about 130 μm; and D10 of about 55 μm to about 85 um.

17. The crystals of claim 1, characterized by a particle size distribution of: D90: about 50 μm to about 100 um; D50: about 20 μm to about 30 μm; and D10 of about 3.5 um to about 9 um.

18. The crystals of claim 1, characterized by a particle size distribution of: D90: about 70 μm to about 95 um; D50: about 25 μm to about 40 μm; and D10 of about 5 μm to about 15 um.

19. The crystals of claim 1, characterized by a particle size distribution of: D90: about 120 μm to about 160 um; D50: about 55 μm to about 85 μm; and D10 of about 5 μm to about 15 um.

20. The crystals of claim 1, characterized by a particle size distribution of: D90: about 90 μm to about 130 um; D50: about 35 μm to about 60 μm; and D10 of about 10 μm to about 15 um.

\* \* \* \* \*